(12) United States Patent　　(10) Patent No.: US 12,616,827 B2

Anstadt　　(45) Date of Patent: May 5, 2026

(54) SYSTEM AND METHOD FOR ASSISTING THE HEART IN PUMPING BLOOD

(71) Applicant: Lifebridge Technologies, LLC, Dayton, OH (US)

(72) Inventor: Mark P. Anstadt, Kettering, OH (US)

(73) Assignee: Lifebridge Technologies LLC, Dayton, OH (US)

(*) Notice: Subject to any disclaimer, the term of this patent is extended or adjusted under 35 U.S.C. 154(b) by 116 days.

(21) Appl. No.: 18/509,260

(22) Filed: Nov. 14, 2023

(65) Prior Publication Data

US 2024/0082566 A1　　Mar. 14, 2024

Related U.S. Application Data

(63) Continuation-in-part of application No. 18/447,786, filed on Aug. 10, 2023, now Pat. No. 12,115,363, and (Continued)

(51) Int. Cl.

| | | |
|---|---|---|
| *A61M 60/191* | (2021.01) | |
| *A61M 60/289* | (2021.01) | |
| (Continued) | | |

(52) U.S. Cl.

CPC ........ *A61M 60/191* (2021.01); *A61M 60/289* (2021.01); *A61M 60/468* (2021.01); (Continued)

(58) Field of Classification Search

CPC ............ A61F 2/2481; A61F 2002/2484; A61F 2250/0003; A61F 2250/0058; (Continued)

(56) References Cited

U.S. PATENT DOCUMENTS

| 2,826,193 A | 3/1958 | Vineberg |
|---|---|---|
| 2,889,780 A | 6/1959 | Binford |
| | (Continued) | |

FOREIGN PATENT DOCUMENTS

| WO | WO 00/78375 | 12/2000 |
|---|---|---|
| WO | WO2005/091860 | 10/2005 |
| WO | WO2006/122036 | 11/2006 |

*Primary Examiner* — Pamela M. Bays

(74) *Attorney, Agent, or Firm* — LaMorte & Associates P.C.

(57) ABSTRACT

A system and method of increasing the pumping efficiency of an individual's heart, wherein an actual pumping efficiency is compared to an optimal pumping efficiency to determine a force assist profile. A cardiac assist device is created that will apply the force assist profile to the heart. The cardiac assist device is surgically inserted in vivo to physically affect the heart. The cardiac assist device has an outer shell and at least one inflatable membrane that passes over the ventricles of the heart, wherein the inflatable membrane is inflated and deflated in accordance with a pressure profile provided by a pneumatic pump. The outer shell embodies outer shell strain characteristics. Each inflatable membrane embodies membrane strain characteristics. The force assist profile is a function of the outer shell strain characteristics, the membrane strain characteristics, and the pressure profile.

8 Claims, 24 Drawing Sheets

Related U.S. Application Data a continuation-in-part of application No. 18/160,963, filed on Jan. 27, 2023, now Pat. No. 11,896,812, and a continuation-in-part of application No. 18/150,746, filed on Jan. 5, 2023, now Pat. No. 12,263,332, which is a continuation-in-part of application No. 17/931, 853, filed on Sep. 13, 2022, application No. 18/509, 260 is a continuation-in-part of application No. 17/825,343, filed on May 26, 2022, which is a continuation-in-part of application No. 17/208,776, filed on Mar. 22, 2021, now Pat. No. 11,383,076.

(60) Provisional application No. 63/086,478, filed on Oct. 1, 2020.

(51) Int. Cl.
| | |
|---|---|
| *A61M 60/468* | (2021.01) |
| *A61M 60/50* | (2021.01) |
| *A61M 60/855* | (2021.01) |
| *A61M 60/90* | (2021.01) |

(52) U.S. Cl.
CPC .......... *A61M 60/50* (2021.01); *A61M 60/855* (2021.01); *A61M 60/90* (2021.01); *A61M 2205/0216* (2013.01); *A61M 2205/3327* (2013.01); *A61M 2210/125* (2013.01); *A61M 2230/005* (2013.01); *A61M 2230/60* (2013.01)

(58) Field of Classification Search
CPC .. A61M 60/00; A61M 60/191; A61M 60/468; A61M 2205/0216; A61M 2210/125; A61M 60/289; A61M 60/50; A61M 60/855; A61M 60/90
See application file for complete search history.

(56) References Cited

U.S. PATENT DOCUMENTS

| | | | |
|---|---|---|---|
| 3,053,249 | A | 9/1962 | Smith |
| 3,233,607 | A | 2/1966 | Bolie |
| 3,279,464 | A | 10/1966 | Kline |
| 3,304,501 | A | 2/1967 | Ruthenberg |
| 3,371,662 | A | 3/1968 | Heid |
| 3,376,863 | A | 4/1968 | Kolobow |
| 3,449,767 | A | 6/1969 | Bolie |
| 3,455,298 | A | 7/1969 | Anstadt |
| 3,478,737 | A | 11/1969 | Rassman |
| 3,513,836 | A | 5/1970 | Sausse |
| 3,587,567 | A | 6/1971 | Schiff |
| 3,590,815 | A | 7/1971 | Schiff |
| 3,613,672 | A | 10/1971 | Schiff |
| 3,674,381 | A | 7/1972 | Schiff |
| 4,048,990 | A | 9/1977 | Goetz |
| 4,192,293 | A | 3/1980 | Asrican |
| 4,281,669 | A | 8/1981 | MacGregor |
| 4,448,190 | A | 5/1984 | Freeman |
| 4,536,893 | A | 8/1985 | Parravicini |
| 4,609,176 | A | 9/1986 | Powers |
| 4,621,617 | A | 11/1986 | Sharma |
| 4,662,358 | A | 5/1987 | Farrar |
| 4,684,143 | A | 8/1987 | Sato |
| 4,957,477 | A | 9/1990 | Lundback |
| 4,979,936 | A | 12/1990 | Stephenson |
| 5,066,111 | A | 11/1991 | Inokuchi |
| 5,089,017 | A | 2/1992 | Young |
| 5,098,369 | A | 3/1992 | Heilman et al. |
| 5,098,442 | A | 3/1992 | Grandjean |
| 5,119,804 | A | 6/1992 | Anstadt |
| 5,131,905 | A | 7/1992 | Grooters |
| 5,156,154 | A | 10/1992 | Valenta, Jr. et al. |
| 5,158,978 | A | 10/1992 | Rubin |
| 5,169,381 | A | 12/1992 | Snyders |
| 5,199,804 | A | 4/1993 | Rimbey et al. |

| | | | |
|---|---|---|---|
| 5,205,722 | A | 4/1993 | Hammond |
| 5,256,132 | A | 10/1993 | Snyders |
| 5,273,518 | A | 12/1993 | Lee et al. |
| 5,322,067 | A | 6/1994 | Prater |
| 5,330,505 | A | 7/1994 | Cohen |
| 5,364,337 | A | 11/1994 | Guiraudon et al. |
| 5,368,451 | A | 11/1994 | Hammond |
| 5,374,287 | A | 12/1994 | Rubin |
| 5,383,840 | A | 1/1995 | Heilman et al. |
| 5,385,528 | A | 1/1995 | Wilk |
| 5,429,584 | A | 7/1995 | Chiu |
| 5,476,502 | A | 12/1995 | Rubin |
| 5,496,353 | A | 3/1996 | Grandjean et al. |
| 5,533,958 | A | 7/1996 | Wilk |
| 5,558,617 | A | 9/1996 | Heilman et al. |
| 5,562,595 | A | 10/1996 | Neisz |
| 5,658,237 | A | 8/1997 | Francischelli |
| 5,674,259 | A | 10/1997 | Gray |
| 5,697,884 | A | 12/1997 | Francischelli et al. |
| 5,697,952 | A | 12/1997 | Francischelli et al. |
| 5,707,336 | A | 1/1998 | Rubin |
| 5,713,954 | A | 2/1998 | Rosenberg et al. |
| 5,716,379 | A | 2/1998 | Bourgeois et al. |
| 5,738,627 | A | 4/1998 | Kovacs et al. |
| 5,749,839 | A | 5/1998 | Kovacs |
| 5,769,800 | A | 6/1998 | Gelfand et al. |
| 5,800,334 | A | 9/1998 | Wilk |
| 5,861,558 | A | 1/1999 | Buhl et al. |
| 5,876,345 | A | 3/1999 | Eaton et al. |
| 5,902,229 | A | 5/1999 | Tsitlik et al. |
| 5,908,378 | A | 6/1999 | Kovacs et al. |
| 5,910,124 | A | 6/1999 | Rubin |
| 5,919,209 | A | 7/1999 | Schouten |
| 5,971,910 | A | 10/1999 | Tsitlik et al. |
| 5,971,911 | A | 10/1999 | Wilk |
| 5,980,571 | A | 11/1999 | Nomura et al. |
| 6,042,532 | A | 3/2000 | Freed et al. |
| 6,044,298 | A | 3/2000 | Salo et al. |
| 6,059,750 | A | 5/2000 | Fogarty et al. |
| 6,076,013 | A | 6/2000 | Brennan et al. |
| 6,095,968 | A | 8/2000 | Snyders |
| 6,110,098 | A | 8/2000 | Renirie et al. |
| 6,123,726 | A | 9/2000 | Mori et al. |
| 6,132,363 | A | 10/2000 | Freed et al. |
| 6,183,412 | B1 | 2/2001 | Benkowski et al. |
| 6,206,820 | B1 | 3/2001 | Kazi et al. |
| 6,224,540 | B1 | 5/2001 | Lederman et al. |
| 6,238,334 | B1 | 5/2001 | Easterbrook, III et al. |
| 6,251,061 | B1 | 6/2001 | Hastings et al. |
| 6,254,525 | B1 | 7/2001 | Reinhardt et al. |
| 6,282,445 | B1 | 8/2001 | Reinhardt et al. |
| 6,298,266 | B1 | 10/2001 | Rubin et al. |
| 6,309,380 | B1 | 10/2001 | Larson et al. |
| 6,328,689 | B1 | 12/2001 | Gonzalez et al. |
| 6,408,205 | B1 | 6/2002 | Renirie et al. |
| 6,432,039 | B1 | 8/2002 | Wardle |
| 6,438,411 | B1 | 8/2002 | Guttman et al. |
| 6,464,655 | B1 | 10/2002 | Shahinpoor |
| 6,485,407 | B2 | 11/2002 | Alferness et al. |
| 6,508,756 | B1 | 1/2003 | Kung et al. |
| 6,540,659 | B1 | 4/2003 | Milbocker |
| 6,547,716 | B1 | 4/2003 | Milbocker |
| 6,572,534 | B1 | 6/2003 | Milbocker et al. |
| 6,602,182 | B1 | 8/2003 | Milbocker |
| 6,612,978 | B2 | 9/2003 | Lau et al. |
| 6,616,596 | B1 | 9/2003 | Milbocker |
| 6,622,045 | B2 | 9/2003 | Snell et al. |
| 6,626,821 | B1 | 9/2003 | Kung et al. |
| 6,641,604 | B1 | 11/2003 | Adelman et al. |
| 6,682,474 | B2 | 1/2004 | Lau et al. |
| 6,730,016 | B1 | 5/2004 | Cox et al. |
| 6,757,561 | B2 | 6/2004 | Rubin et al. |
| 6,808,483 | B1 | 10/2004 | Ortiz et al. |
| 6,846,296 | B1 | 1/2005 | Milbocker et al. |
| 6,971,127 | B2 | 12/2005 | Richards |
| 7,331,221 | B2 | 2/2008 | Wise et al. |
| 7,494,459 | B2 | 2/2009 | Anstadt et al. |
| 7,871,366 | B2 | 1/2011 | Criscione et al. |
| 8,187,160 | B2 | 5/2012 | Criscione et al. |

(56)                References Cited

U.S. PATENT DOCUMENTS

| | | | |
|---|---|---|---|
| 8,460,161 B2 | 6/2013 | Saadat et al. | |
| 8,460,181 B2 | 6/2013 | Saadat et al. | |
| 10,463,496 B2 | 11/2019 | Criscione et al. | |
| 11,191,944 B2 | 12/2021 | Tuval et al. | |
| 11,511,102 B2 | 11/2022 | Criscione et al. | |
| 12,115,363 B1 | 10/2024 | Anstadt | |
| 12,161,857 B2 | 12/2024 | Saul et al. | |
| 2001/0002445 A1 | 5/2001 | Vesely et al. | |
| 2001/0041821 A1 | 11/2001 | Wilk | |
| 2002/0173693 A1 | 11/2002 | Landesberg | |
| 2003/0032855 A1 | 2/2003 | Shahinpoor | |
| 2004/0010180 A1 | 1/2004 | Scorvo | |
| 2004/0024315 A1 | 2/2004 | Chalana | |
| 2004/0059183 A1 | 3/2004 | Jozef et al. | |
| 2004/0078067 A1 | 4/2004 | Thompson et al. | |
| 2004/0102674 A1 | 5/2004 | Zadini et al. | |
| 2004/0116769 A1 | 6/2004 | Jassawalla | |
| 2004/0167375 A1 | 8/2004 | Couvillon | |
| 2004/0225177 A1 | 11/2004 | Coleman et al. | |
| 2004/0267086 A1 | 12/2004 | Anstadt | |
| 2005/0113632 A1 | 5/2005 | Ortiz et al. | |
| 2005/0148814 A1 | 7/2005 | Fischi et al. | |
| 2005/0234289 A1 | 10/2005 | Anstadt et al. | |
| 2006/0106442 A1 | 5/2006 | Richardson et al. | |
| 2006/0129025 A1 | 6/2006 | Levine et al. | |
| 2006/0142634 A1* | 6/2006 | Anstadt | A61M 60/515 600/16 |
| 2006/0167334 A1 | 7/2006 | Anstadt et al. | |
| 2006/0211909 A1 | 9/2006 | Anstadt et al. | |
| 2007/0197859 A1 | 8/2007 | Schaer et al. | |
| 2008/0255629 A1 | 10/2008 | Jenson | |
| 2008/0257412 A1 | 10/2008 | Gordon | |
| 2009/0036730 A1* | 2/2009 | Criscione | A61M 60/468 600/37 |
| 2009/0099498 A1 | 4/2009 | Demers et al. | |
| 2010/0081867 A1 | 4/2010 | Fishler | |
| 2010/0152523 A1 | 6/2010 | MacDonald et al. | |
| 2010/0191071 A1 | 7/2010 | Anderson | |
| 2011/0196189 A1 | 8/2011 | Milbocker | |
| 2012/0095498 A1 | 4/2012 | Stefanchik et al. | |
| 2013/0102849 A1 | 4/2013 | Criscione | |
| 2015/0018607 A1 | 1/2015 | Akita | |
| 2015/0080640 A1 | 3/2015 | Lillehei | |
| 2016/0101230 A1 | 4/2016 | Ochsner | |
| 2016/0151552 A1 | 6/2016 | Solem | |
| 2016/0262889 A1 | 9/2016 | Laham et al. | |
| 2016/0346449 A1* | 12/2016 | Roche | A61M 60/289 |
| 2017/0258593 A1 | 9/2017 | Good et al. | |
| 2018/0153709 A1 | 6/2018 | Hunter | |
| 2019/0224395 A1 | 7/2019 | Pilla et al. | |
| 2020/0085579 A1 | 3/2020 | Kim | |
| 2022/0013211 A1 | 1/2022 | Steinberg | |
| 2022/0249830 A1 | 8/2022 | Kanz | |
| 2023/0060284 A1 | 3/2023 | Siess et al. | |
| 2023/0071248 A1 | 3/2023 | Keenan et al. | |
| 2024/0216652 A1 | 7/2024 | Keenan et al. | |
| 2024/0269459 A1 | 8/2024 | Schellenberg et al. | |

* cited by examiner

SYSTEM AND METHOD FOR ASSISTING THE HEART IN PUMPING BLOOD

RELATED APPLICATIONS

This application is a continuation-in-part of co-pending U.S. application Ser. No. 17/825,343 filed May 26, 2022, which is a continuation-in-part of U.S. application Ser. No. 17/208,776 filed Mar. 22, 2022, now U.S. Pat. No. 11,383, 076, which claimed priority of U.S. Provisional Application No. 63/086,478 filed Oct. 1, 2020.

This application is also a continuation-in-part of U.S. application Ser. No. 18/150,746 filed Jan. 5, 2023, which is a continuation-in-part of U.S. application Ser. No. 17/931, 853 filed Sep. 13, 2022, now U.S. Pat. No. 12,263,332.

This application is a further continuation-in-part of U.S. patent application Ser. No. 18/160,963, filed Jan. 27, 2023, now U.S. Pat. No. 11,869,812.

This application is yet a further continuation-in-part of U.S. application Ser. No. 18/447,786 filed Aug. 10, 2023, now U.S. Pat. No. 12,115,363.

BACKGROUND OF THE INVENTION

1. Field of the Invention

In general, the present invention relates to cardiac assist systems and methods that help the heart pump blood by applying forces to the exterior of the heart. More particularly, the present invention relates to the structure of the cardiac assist systems and their methods of operation.

2. Prior Art Description

There are many instances when a heart needs assistance to maintain a proper blood flow in a patient. Often hearts that are diseased, failing, or have stopped need the application of a cardiac assist system to prevent a patient from dying. Furthermore, the proper mechanical massaging of the failing heart may have additional therapeutic implications for recovery. In the prior art, many cardiac assist systems pierce the heart and/or vascular system so as to have direct effect upon the patient's blood. However, thromboembolic events, the need for anticoagulation, hemolysis, immune reactions, and infections, contribute significantly to morbidity and mortality of such cardiac assist systems. Accordingly, it is preferable that the pumping of the heart be assisted not by directly acting upon the blood but by applying forces to the external surfaces of the heart as the heart expands and contracts. In this manner, the heart pumps the blood without having to interrupt the natural flow of the blood. Furthermore, the proper force applications to the external surfaces of the heart may aid in the heart's recovery.

In the prior art, there are many constructs that surround the ventricles of the heart and apply forces to the ventricles. Such systems are typically designed to help the ventricles of the heart to empty. However, the heart is a complex organ that both empties and fills as it pumps. In order for a heart to pump blood effectively and efficiently, a heart often needs assistance in both filling and emptying. Additionally, proper mechanical forces applied to the heart which still has some pumping function can aid in the heart's diastolic and systolic function and facilitate more physiologic heart function during filling and emptying cycles of a heart.

In U.S. Pat. No. 3,455,298, Dr. George Anstadt introduced a cardiac assist device that assists a heart in both its systolic and diastolic cycles. The device, known in the medical industry as the Anstadt cup, is a cup-shaped construct that fits over the ventricles of the heart. The Anstadt cup has a stiff outer shell and an inflatable inner membrane. The outer shell and inflatable membrane are placed around the ventricles of the heart. When the inflatable membrane expands, the inflatable membrane compresses the heart, therein helping with the heart's emptying or its systolic function when native heart function is still present. When the membrane deflates, there is a negative pressure that is created between the tissue of the heart and the stiff outer shell. This negative pressure assists the heart in filling, or with its diastolic pump function, when native heart function is still present.

Although the Anstadt cup does assist in the heart's pump function, the assist is less than optimal. Likewise, since the inflatable membrane is positioned between a rigid shell and the heart, the forces that can be applied to the heart are not nuanced. When the heart has an inherent pump function, the heart does more than fill and empty. During the pumping cycle, the heart also elongates and contracts. Likewise, ventricular tissue also twists as it expands and contracts. A cardiac assist device that uses a rigid shell and non-ideal membrane characteristics has very limited ability to follow the heart surface as the heart elongates, contracts and/or twists. This is important to conditions where the heart has no pump function and is changing its conformation in response to the device's forces, as well as when the heart is exhibiting inherent pump function and the device is aiding in promoting physiologic diastolic and systolic pump function. As a result, some areas of the heart experience higher surface forces than they should be, and some areas experience less surface forces than they should be. The result is an application of forces that are a compromise between what is mechanically achievable and what is needed to properly follow the heart's natural strain dynamics during filling and emptying.

Computer imaging software has allowed intricate three dimensional understanding of the heart conformational changes which can be characterized in three dimensional strain analyses. In a similar manner, material strain characteristics of a device can be analyzed and constructed to best act on the heart's surface. The interactions of a device and the heart can then be further analyzed such as the displacements imposed on the heart tissue by forces from the device as the material interacts with the heart surface. What is needed is a device construct having membrane fixing behavioral properties, housing framework properties, and drive system regulation that combine to generate ideal compression and expansion forces over the heart's surface. The combined ideal effect of a cardiac assist device construct can then be further refined through controlling forces delivered by the drive system which can adjust for physiologic changes imposed by the cardiovascular system. While assumptions may be used to model such a cardiac system, they can significantly deviate from reality in the physiologic setting. The discoveries revealed in this patent application pertain to the identity of the most ideal strain characteristics of the device construct's shell and outer membrane that allow the heart to be mechanically compressed and expanded when driven by an appropriate drive system. The discovered ideal strain characteristics can be objectively measured with respect to loads or forces delivered from the drive system when the device is not acting on the heart. The discovered ideal strain characteristics can also be objectively measured with respect to the loads delivered by the drive system while the device is acting on the heart or a model of the cardiovascular system. The discovered strain characteristics of the device construct can be defined using 3-dimensional analysis in either loaded or unloaded conditions. However, characterization in either one or two dimensional planes provides reasonable surrogates for more practical, objective strain analyses.

A need therefore exists for an improved cardiac assist system that has a flexible outer shell integrated with an ideal inner membrane which combine to optimize the filling and emptying forces applied to the heart's surface. In this manner, the forces applied to the heart can result in optimal pump function of the arrested heart as well as better assist the heart's native pump function and best enable the potential recovery of heart function. This need is met by the present invention as described and claimed below.

SUMMARY OF THE INVENTION

The present invention is a system and method of increasing the pumping efficiency of an individual's heart. The heart is scanned in vivo to determine an actual pumping efficiency for the heart. The actual pumping efficiency is compared to an optimal pumping efficiency of an equivalent healthy heart to determine a force assist profile. The force assist profile is the force profile that, if physically applied to the individual's heart, would assist the heart in pumping blood at an improved efficiency that is closer to the optimal pumping efficiency.

A cardiac assist device is created that will apply the force assist profile to the heart. The cardiac assist device is surgically inserted in vivo to physically affect the heart. The cardiac assist device embodies materials that exhibit strain characteristics during its elongation and shortening that facilitate the compression and expansion of the heart. The cardiac assist device utilizes material dynamics needed to track the heart's surface such that the strain dynamics of the cardiac assist device are optimized for the needs of the heart. This allows the cardiac assist device to foster the heart's natural conformational changes during compression and expansion and facilitates the cardiac assist device's ability to grip the heart during transfer of the compression and expansion forces imposed over the heart's surface. The cardiac assist device has an outer shell and at least one inflatable membrane that passes over the ventricles of the heart, wherein the inflatable membrane is inflated and deflated in accordance with a pressure profile provided by a pneumatic pump.

The outer shell embodies outer shell strain characteristics that are a function of dimensions and materials utilized by the outer shell. Each inflatable membrane embodies membrane strain characteristics that are a function of dimensions and materials utilized by the inflatable membrane. The force assist profile is a function of forces that are applied by the outer shell and the elastic inflatable membranes when acted upon the drive system pressure profile and the heart.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention cardiac assist system and methodology can be embodied in many ways, only some exemplary embodiments are illustrated and described. The exemplary embodiments are being shown for the purposes of explanation and description. The exemplary embodiments are selected in order to set forth some of the best modes contemplated for the invention. The illustrated embodiments, however, are merely exemplary and should not be considered as limitations when interpreting the scope of the appended claims.

Figure 1:
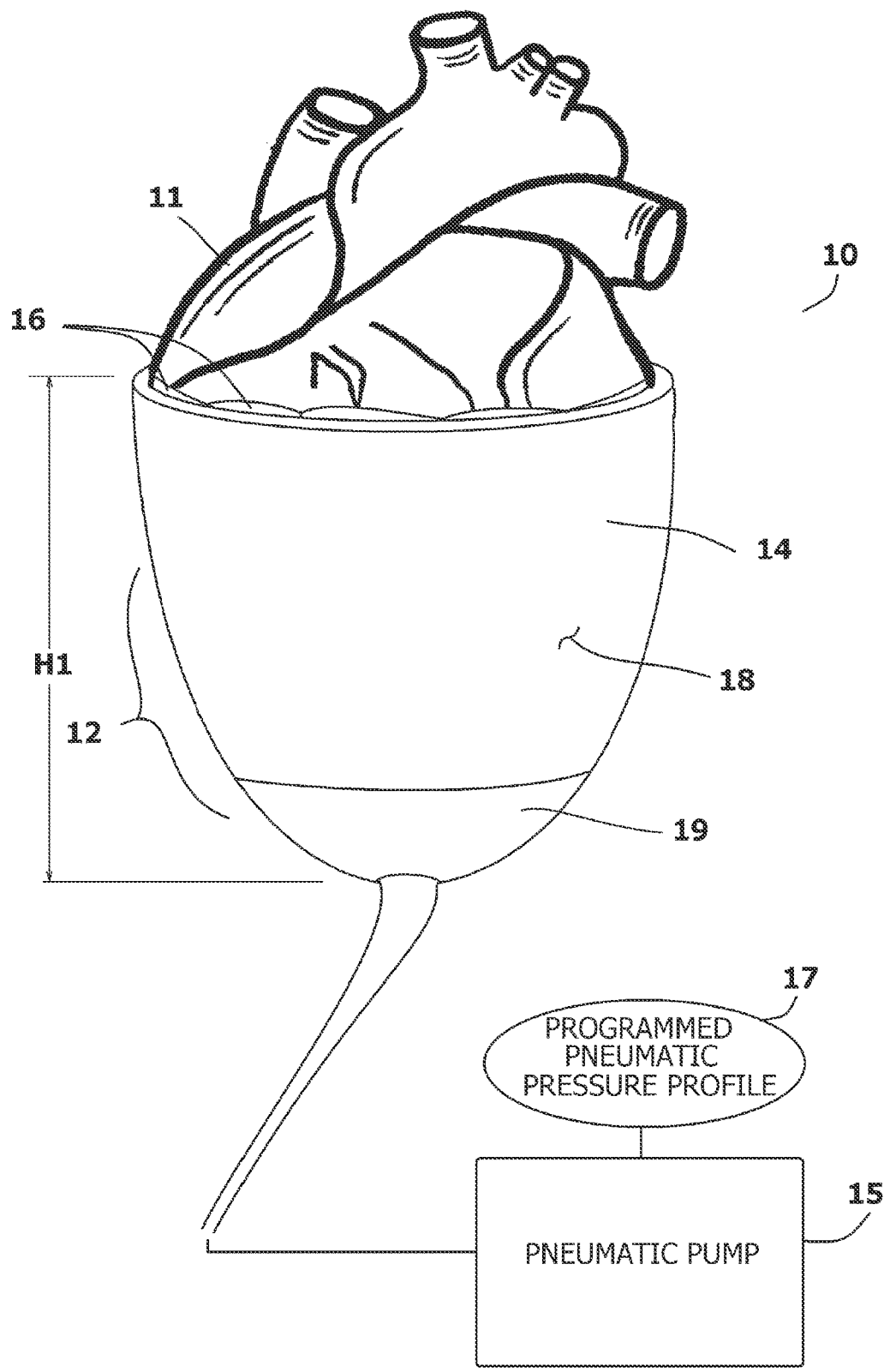
FIG. 1 shows an exemplary embodiment of a cardiac assist system engaging a heart.
Figure 2:
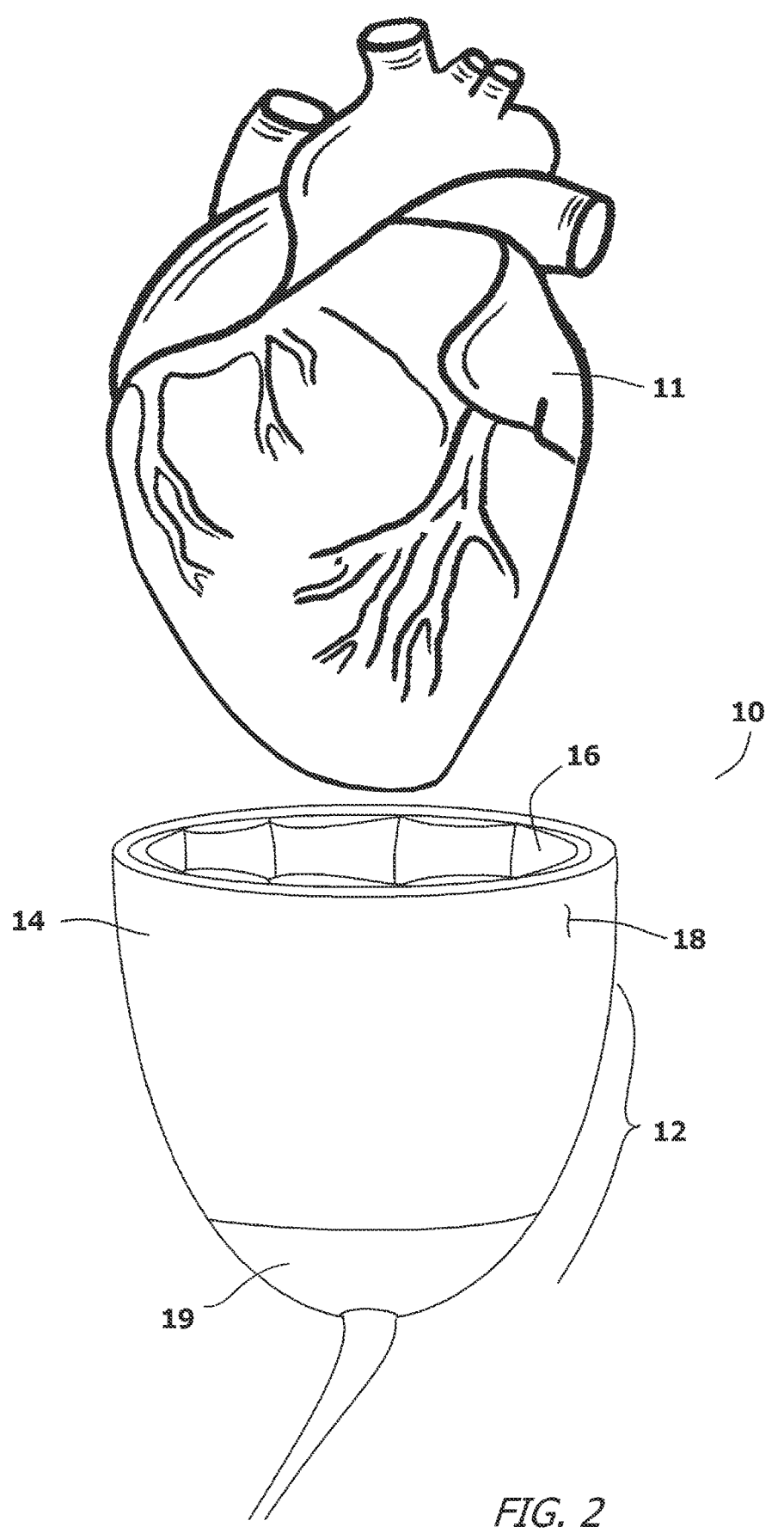
FIG. 2 shows the cardiac assist system of FIG. 1 with the cardiac assist system separated from the heart.

Referring to FIG. 1 and FIG. 2, an improved cardiac assist system 10 is shown in conjunction with a heart 11. The cardiac assist system 10 contains a cup assembly 12. The cup assembly 12 includes an outer shell 14 that is internally lined with one or more inflatable membranes 16. The outer shell 14 is set upon a base 19 to complete the cup assembly 12. The complete cup assembly 12 has an overall height H1 from the apex of the base 19 to the top opening. The height of the base 19 is between 25 percent and 35 percent of the overall height H1. Accordingly, the height of the outer shell 14 is between 65 percent and 75 percent of the height H1 of the cup assembly 12.

The inflatable membranes 16 are attached to the interior of the outer shell 14 along a basal bond and an apical bond. The inflatable membranes 16 begin at the apical bond and extend upwardly to the basal bond. The center of the inflatable membrane 16 between the basal bond and the apical bond is considered the long axis of the inflatable membrane 16. The center of the inflatable membrane 16 perpendicular to the long axis is considered the short axis of the inflatable membrane 16. The basal bond attachment point is approximately at a distance below the open top of the cup assembly 12 that is approximately zero percent to five percent of the overall height H1. The inflatable membranes 16 are fabricated to embody specific strain characteristics that can be further customized to the needs of a particular patient's heart. The structure of the inflatable membranes 16 is described in co-pending U.S. patent application Ser. No. 18/150,746, the disclosure of which is herein incorporated by reference.

The inflatable membranes 16 are inflated by a pneumatic pump 15. The pneumatic pump 15 is programable and is supplied with a pressure profile 17. The programable pressure profile 17 inflates and deflates the membranes 16 in accordance with the best regular natural pumping rhythm of the heart 11, or with a best regular pumping rhythm should the heart 11 have stopped. The synchronization of the programable pressure profile 17 to the natural rhythm of a heart is disclosed in co-pending U.S. patent application Ser. No. 17/825,343 the disclosure of which is incorporated herein by reference.

One improvement embodied by the current cardiac assist system 10 is that the outer shell 14 is flexible and is made from elastomeric material 18. Accordingly, the outer shell 14 has the ability to elastically expand, contract, elongate, shorten and twist. The outer shell 14 has an annular shape with an unstressed inner diameter. The maximum width of the unstressed inner diameter of the outer shell 14 is selected to be approximately five percent larger than the maximum atrioventricular diameter of the heart 11. The elastomeric construction of the outer shell 14 enables the outer shell 14 to expand, contract, lengthen and shorten in response to physiologic changes in the cardiovascular system that alter blood pressure and flow seen within the heart. This better enables the outer shell 14 to facilitate the inflatable membranes 16 as the inflatable membranes 16 contract, expand, shorten, lengthen, and twist with the underlying heart 11 as they move through a heart pumping cycle.

Figure 3:
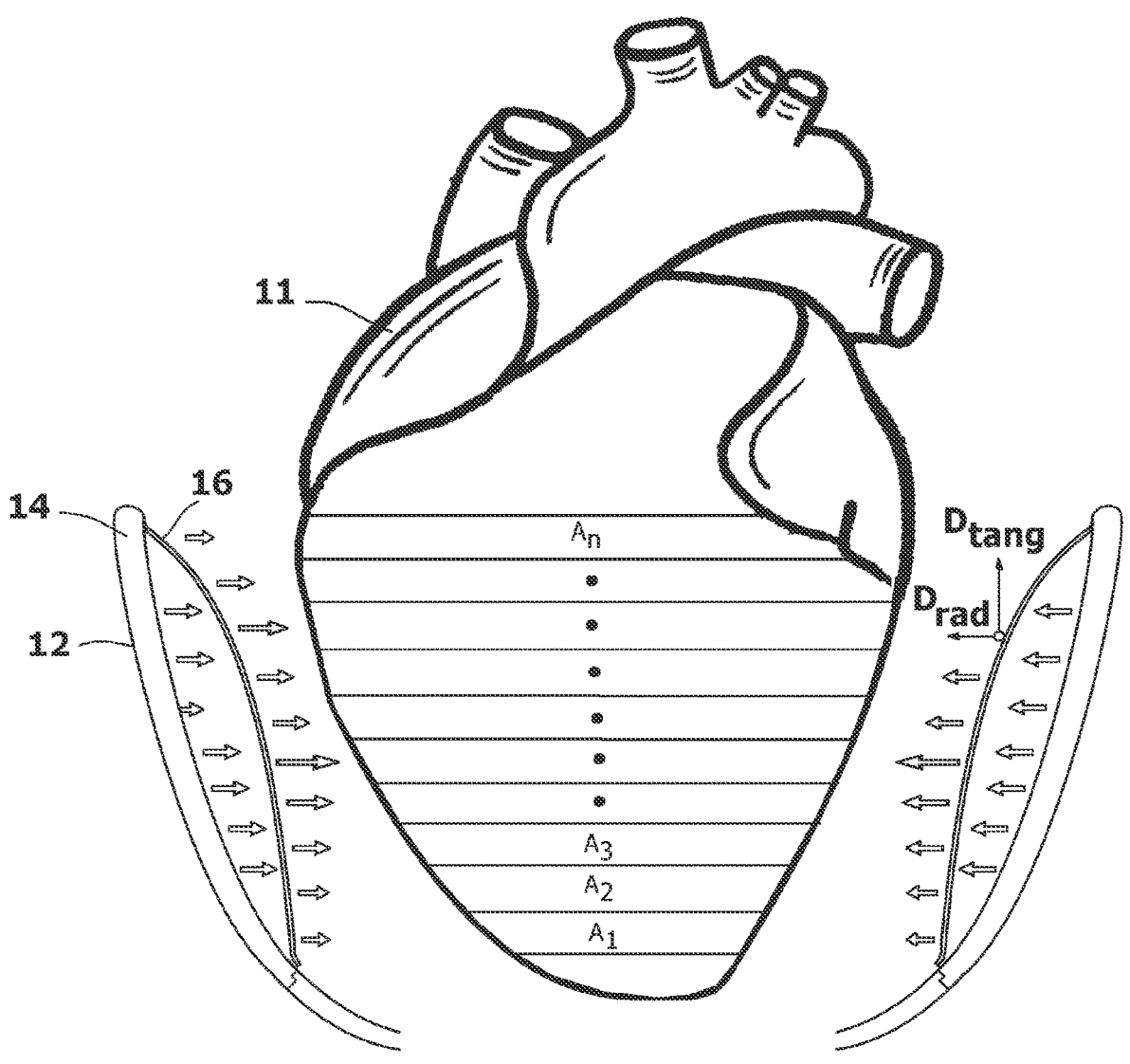
FIG. 3 shows the directional forces applied to the heart by the cardiac assist system used to facilitate the heart emptying or systolic pump function.
Figure 4:
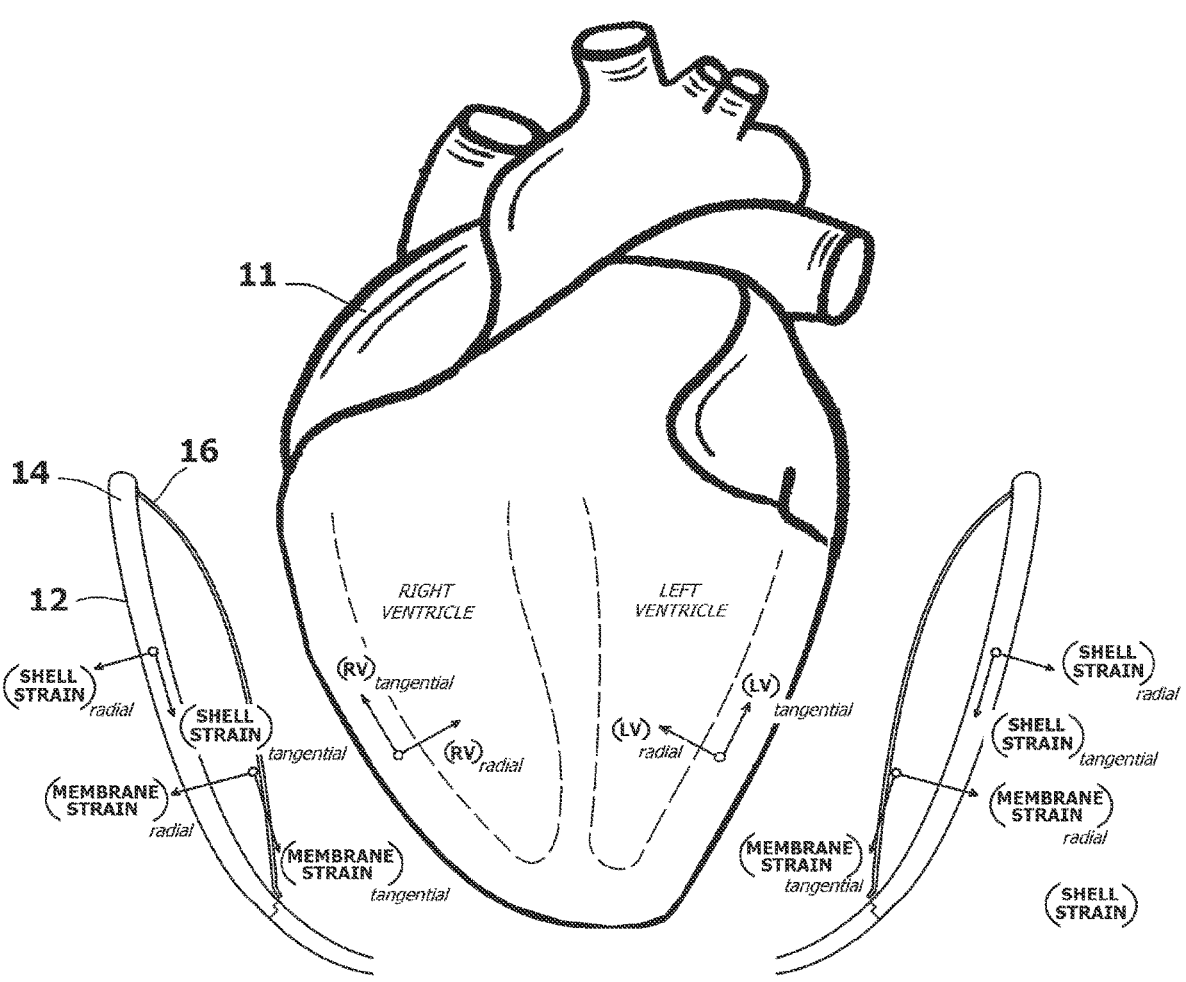
FIG. 4 shows some directions of tangential and radial strain as a loaded cardiac assist system engages a heart during the systolic cycle.

Referring to FIG. 3 and FIG. 4, in conjunction with FIG. 1 and FIG. 2, it will be understood that when the cup assembly 12 is placed around the ventricles of the heart 11, there are multidirectional forces, resulting in multidirectional force dynamics, applied to the heart 11. The force dynamics that are applied to the heart include the forces being applied by each inflatable membrane 16 and the secondary force dynamics being applied by the elastic outer shell 14. Furthermore, the outer shell 14 is designed to embody strain characteristics that complement those of the inflatable membranes 16. In this manner, the compound forces applied to the heart 11 by both the inflatable membranes 16 and the outer shell 14 can be better customized for the needs of the heart 11. If the inflatable membranes 16 act upon only part of the heart 11, as is shown, the inflatable membranes 16 create both direct displacement and indirect displacement of the heart tissue. Direct displacement is created by the forces applied directly to the heart 11 by the inflatable membranes 16. These direct forces compress the heart 11. This direct compression, in turn, causes displacement in adjacent heart tissue that is in contact with the other basal and apical regions of the cup assembly 12. This indirect displacement also alters the shape and volume of the heart 11 and can cause changes in the heart pump cycle.

The dynamics of heart contraction and expansion are highly complex. Different areas of the heart 11 expand and contract to different degrees at different times. In FIG. 3, different areas $(A_1\text{-}A_n)$ of the heart are shown. These different areas $(A_1\text{-}A_n)$ of the heart 11 contraction and expansion occur at different degrees and at different times during the systolic and diastolic of the heart pumping cycle. If the heart 11 is diseased, damaged, drugged or otherwise impaired, the heart 11 may need assistance provided by the cardiac assist system 10. However, for the heart 11 to pump at optimal efficiency, each area $(A_1\text{-}A_n)$ of the heart 11 has an optimal force profile applied. Using the cardiac assist system 10, the compound forces applied to the heart 11 in any area $(A_1\text{-}A_n)$ at any time (t) is equal to the positive/negative forces applied by the membranes 16 plus the positive/negative forces applied by the outer shell 14 at that time. These force dynamics can reverse directions so as to assist the heart 11 in filling or expanding and emptying or contracting at different times.

Figure 5:
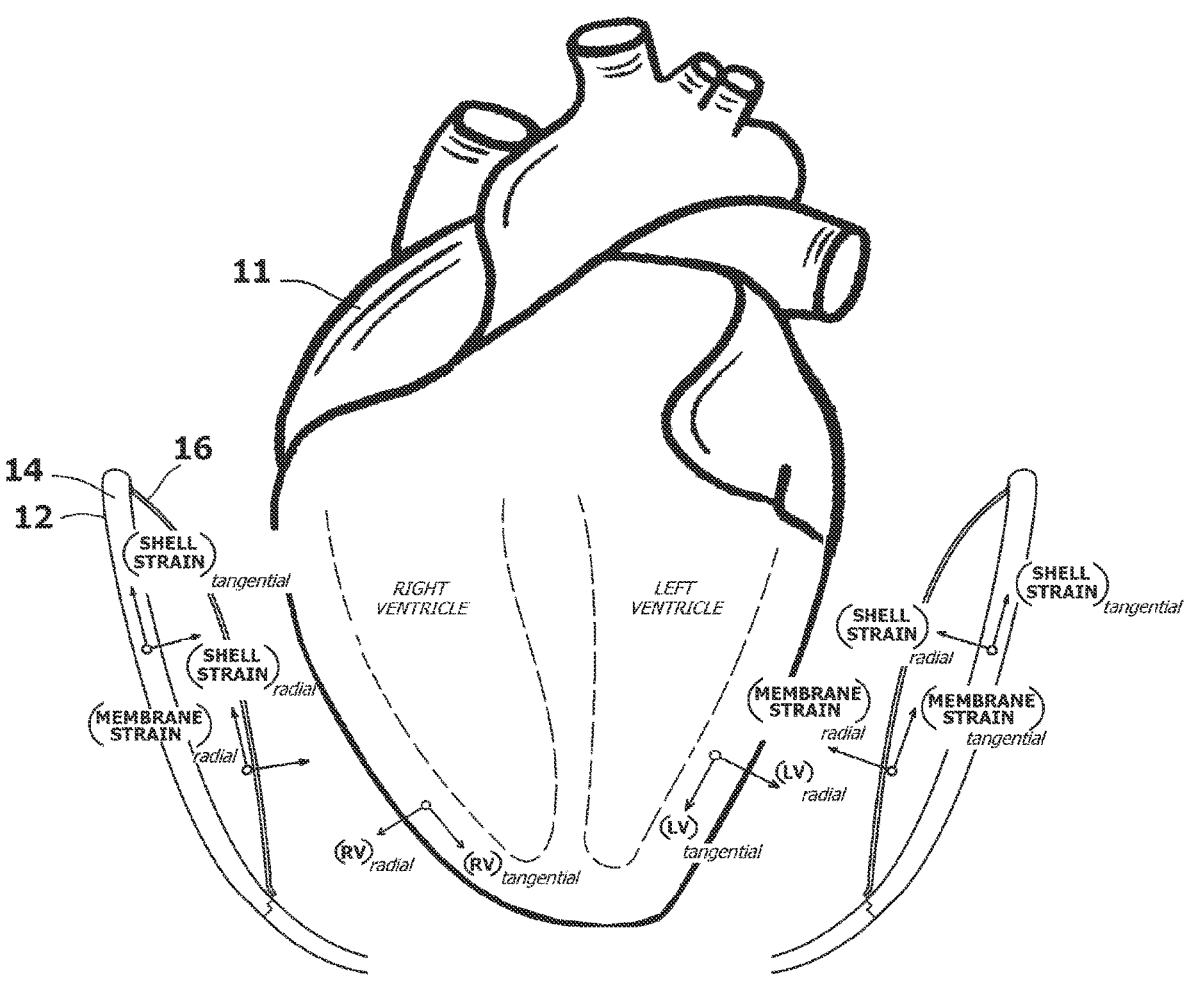
FIG. 5 shows some directions of tangential and radial strain as a loaded cardiac assist system engages a heart during the diastolic cycle.

Referring to FIG. 4 and FIG. 5, it can be seen that when the cup assembly 12 is applied to the heart 11, the cup assembly 12 is under load. The left ventricle and the right ventricle require compound force assistance (i.e. force dynamics) which are functions of strain in the tangential, radial, and circumferential directions. Strain characteristics are usually measured in one or two directions or planes of the heart. The most common measures of strain for these purposes are either in the long or short axis. The flexible membrane 16 embodies various strain characteristics in the radial and tangential directions. Likewise, the outer shell 14 embodies additional strain characteristics in the radial and tangential directions. Together, the strain characteristics embodied by both the outer shell 14 and the inflatable membrane 16 can be customized to assist the heart 11 to fill and empty more effectively, should different disease states require. The ideal strain characteristics discovered in this application relate to a generally normal sized human heart with generally normal anatomic features and construct.

Figure 6:
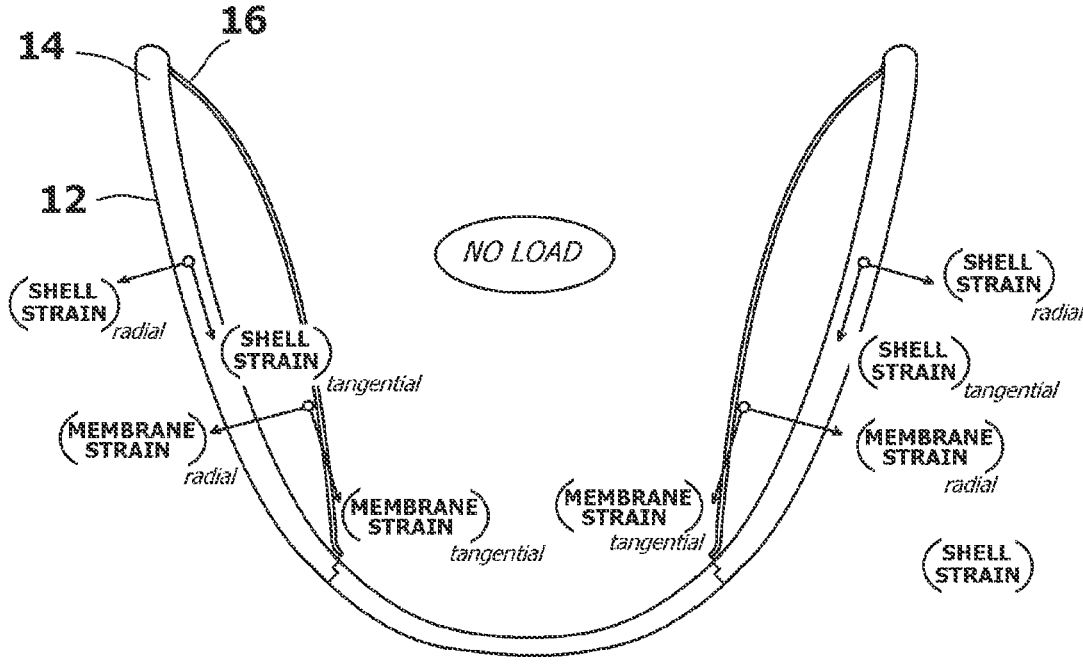
FIG. 6 shows some directions of tangential and radial strain as an unloaded cardiac assist system during inflation of the device.

Referring to FIG. 6, the cup assembly 12 is shown unloaded. That is, the cup assembly 12 is not engaging a heart. In this case, the inflatable membrane 16 inflates to its maximum size at the pressure of 50 mm Hg. The degrees of displacement in the inflatable membranes 16 and the outer shell 14 are later referenced in graphs of the radial and longitudinal tangential axes to illustrate the degree of displacement characteristics needed in an unloaded condition to produce the needed strain characteristics to assist the heart when in a loaded condition.

The forces applied by the inflatable membranes 16 are directly applied to the exterior surface of the heart 11. The force dynamics applied by each inflatable membrane 16 is determined by the strain characteristics of the inflatable membrane 16 and the pressure profiles of the pneumatics being supplied to the inflatable membranes 16. The strain characteristics of the inflatable membrane 16 are also determined by the shape, size, material, and wall thicknesses of the membranes, as described in co-pending U.S. patent application Ser. No. 18/160,963, which has previously been incorporated by reference.

Figure 7:
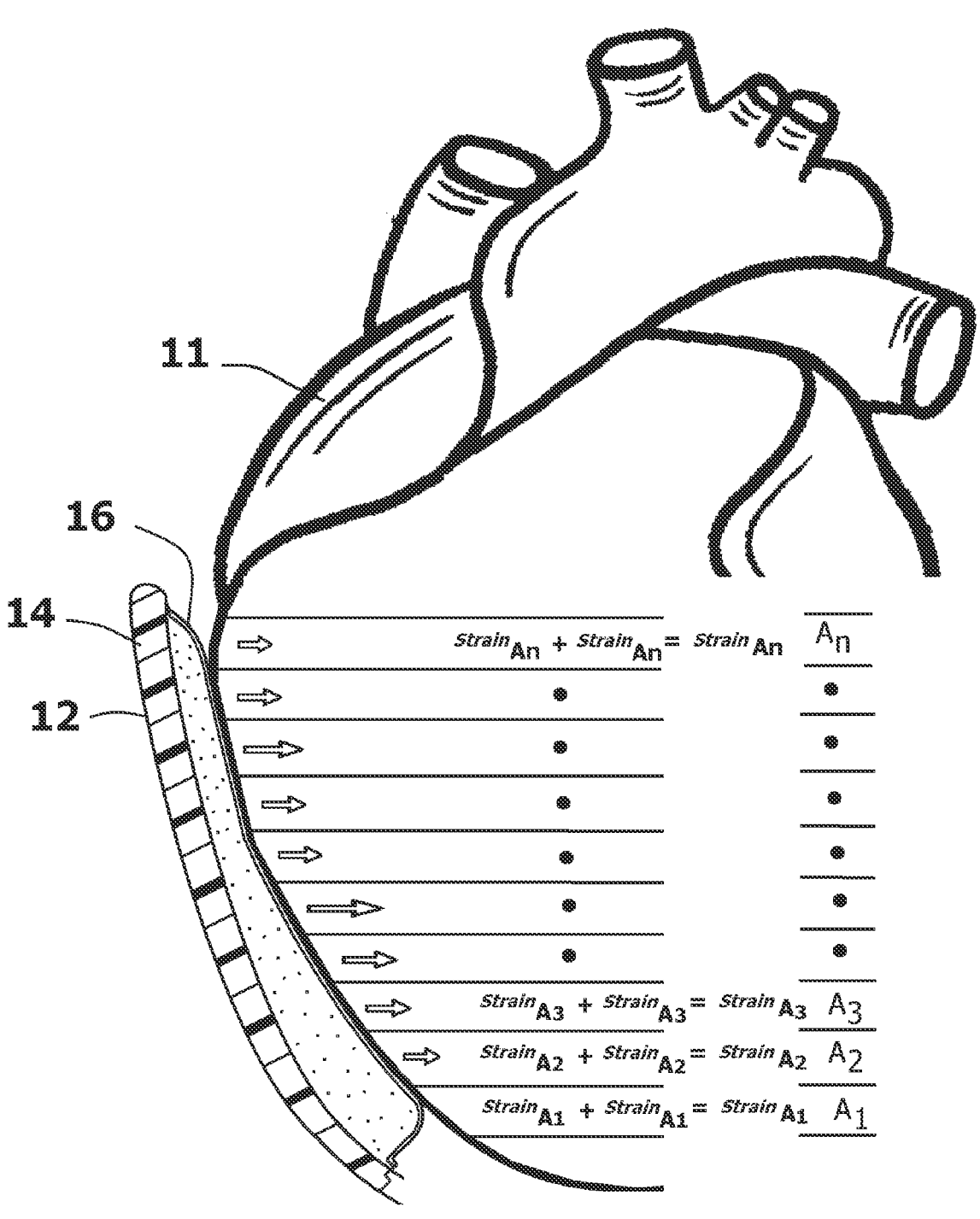
FIG. 7 exemplifies the sum of the composite forces being applied to the heart by the cardiac assist system used to facilitate the heart emptying or systolic pump function.

Referring to FIG. 7, it will now be understood that when the inflatable membranes 16 are inflated and deflated, the inflatable membranes 16 stretch and contract. The strain profile embodied by the inflatable membranes 16 can be characterized in the radial or tangential directions along the long axis and short axis. The degrees of displacement are complex and depend primarily upon the pressure profile provided to the inflatable membrane 16 at any given time combined with the strain characteristics of the inflatable membrane 16. Likewise, the outer shell 14 stretches and contracts in radial and tangential directions along its long axis and short axis. Together, the combined strain characteristics result in complex forces that act upon the heart 11 to assist the heart 11 to both fill and empty effectively.

Figure 8:
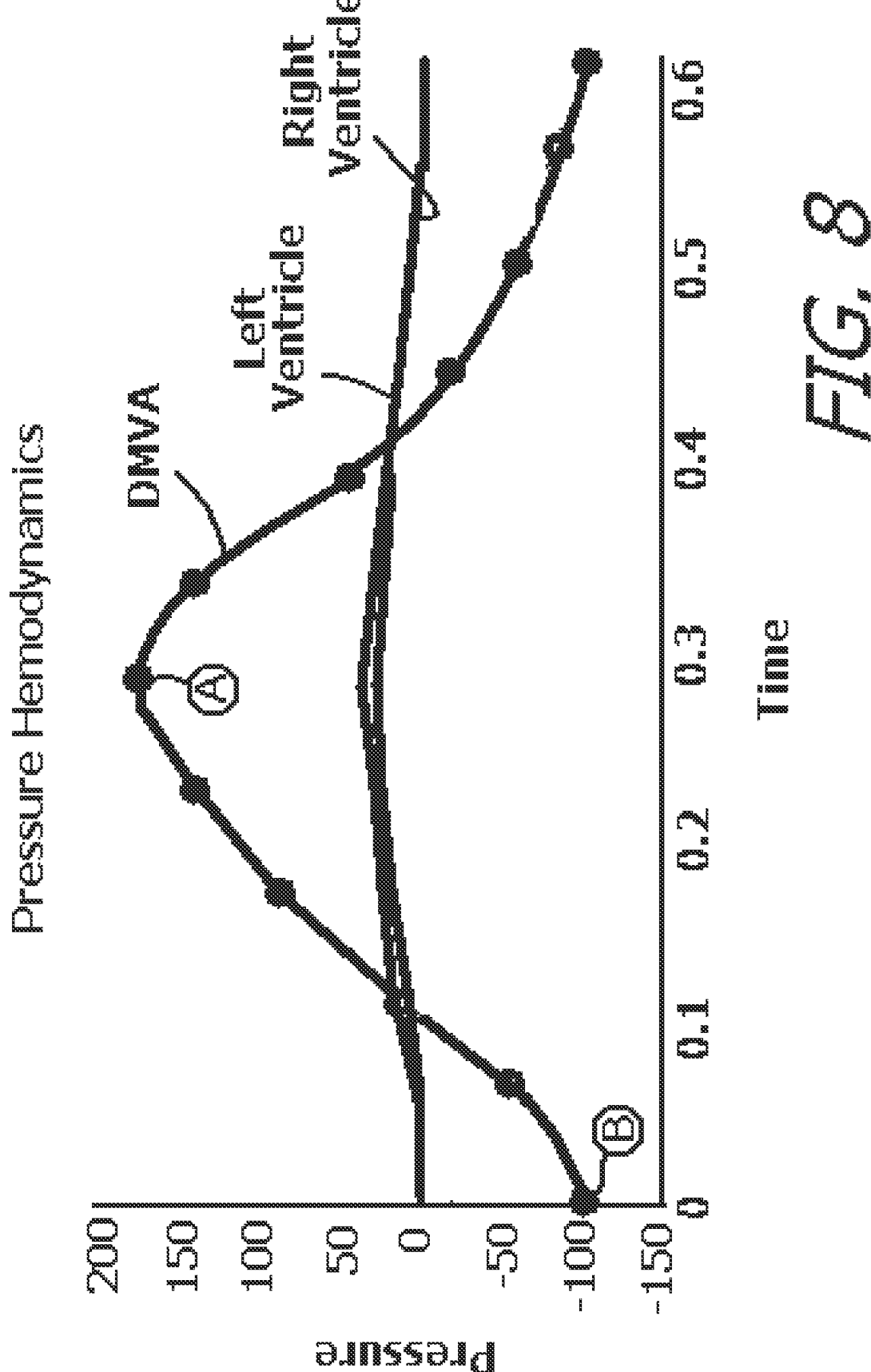
FIG. 8 is a graph that plots pressures versus time for Direct Mechanical Ventricular Activation (DMVA) pneumatic pressure within the device, the heart's left ventricular and right ventricular intra-cavitary pressures as measured on a model of the circulatory system.
Figure 9:
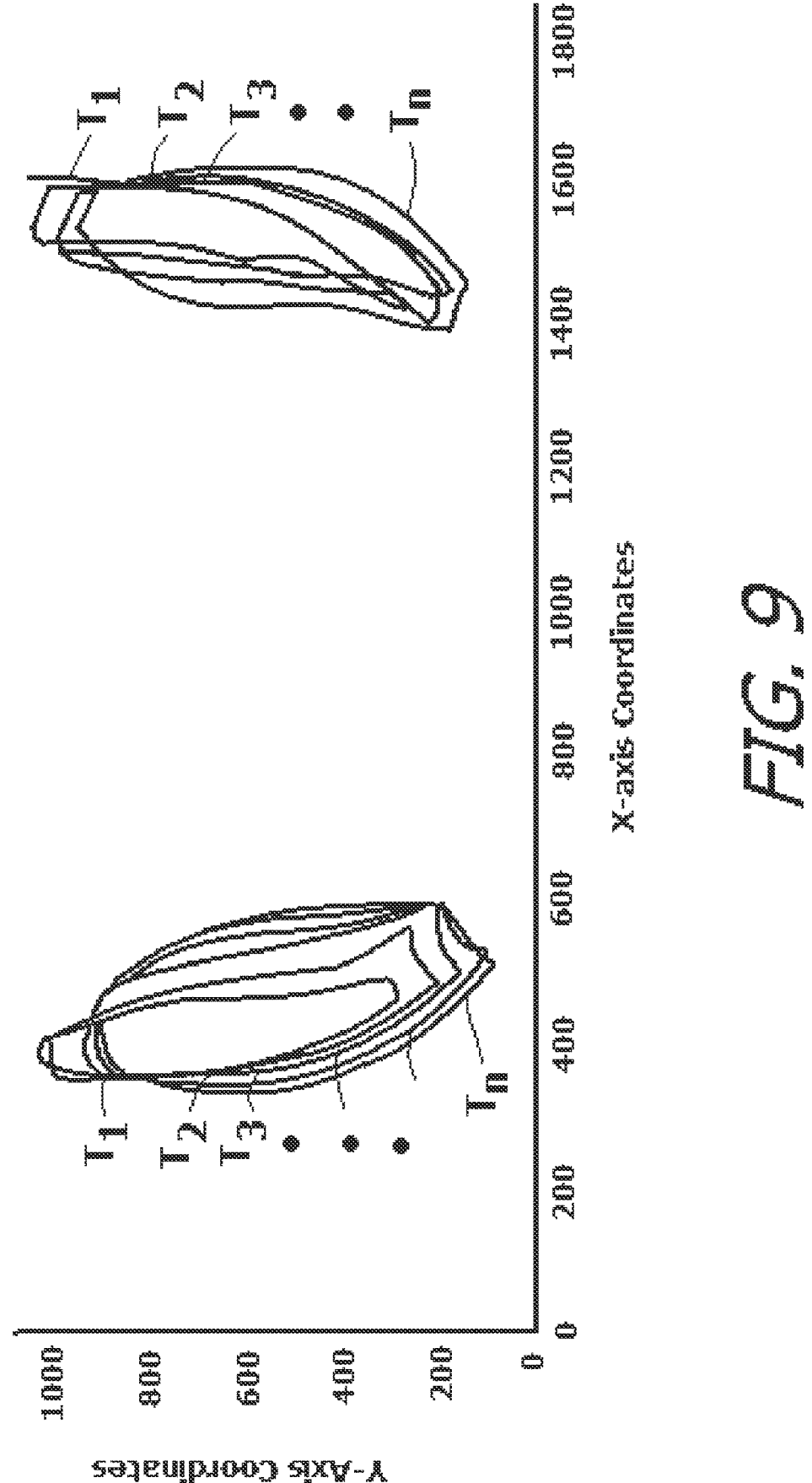
FIG. 9 shows a displacement profile for the device's outer shell and inner membranes along the left ventricle (left side of figure) and right ventricle walls (right side of figure) that illustrates the range of strain characteristics of the device construct as measured two-dimensionally in these regions on a model of the circulatory system.
Figure 10:
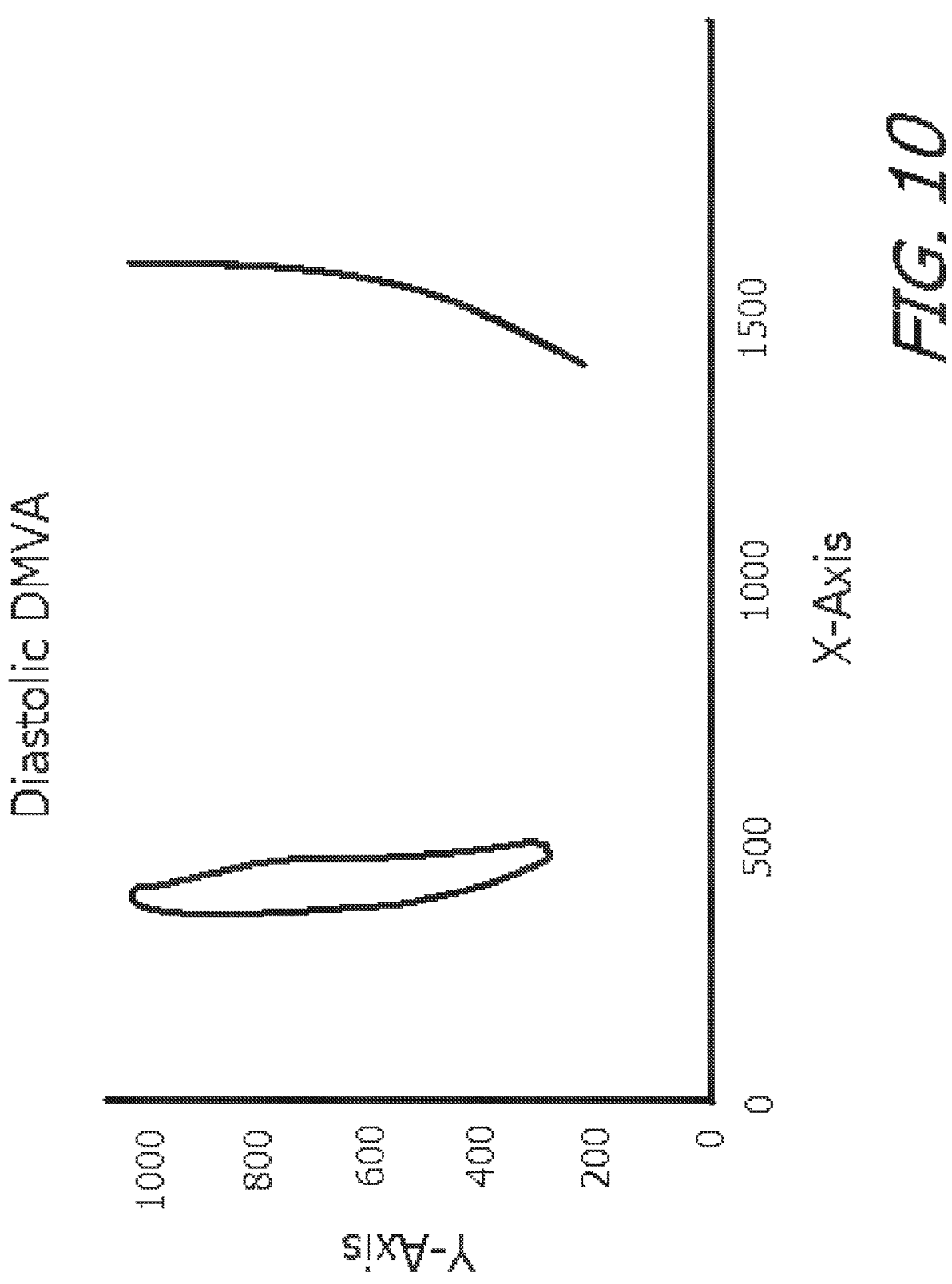
FIG. 10 shows a displacement profile for an exemplary time point along the left ventricle's wall (left side of figure) and the right ventricle's wall (right side of figure) at the end of the diastolic or filling portion of the heart's pump function in a model of the circulatory system.
Figure 11:
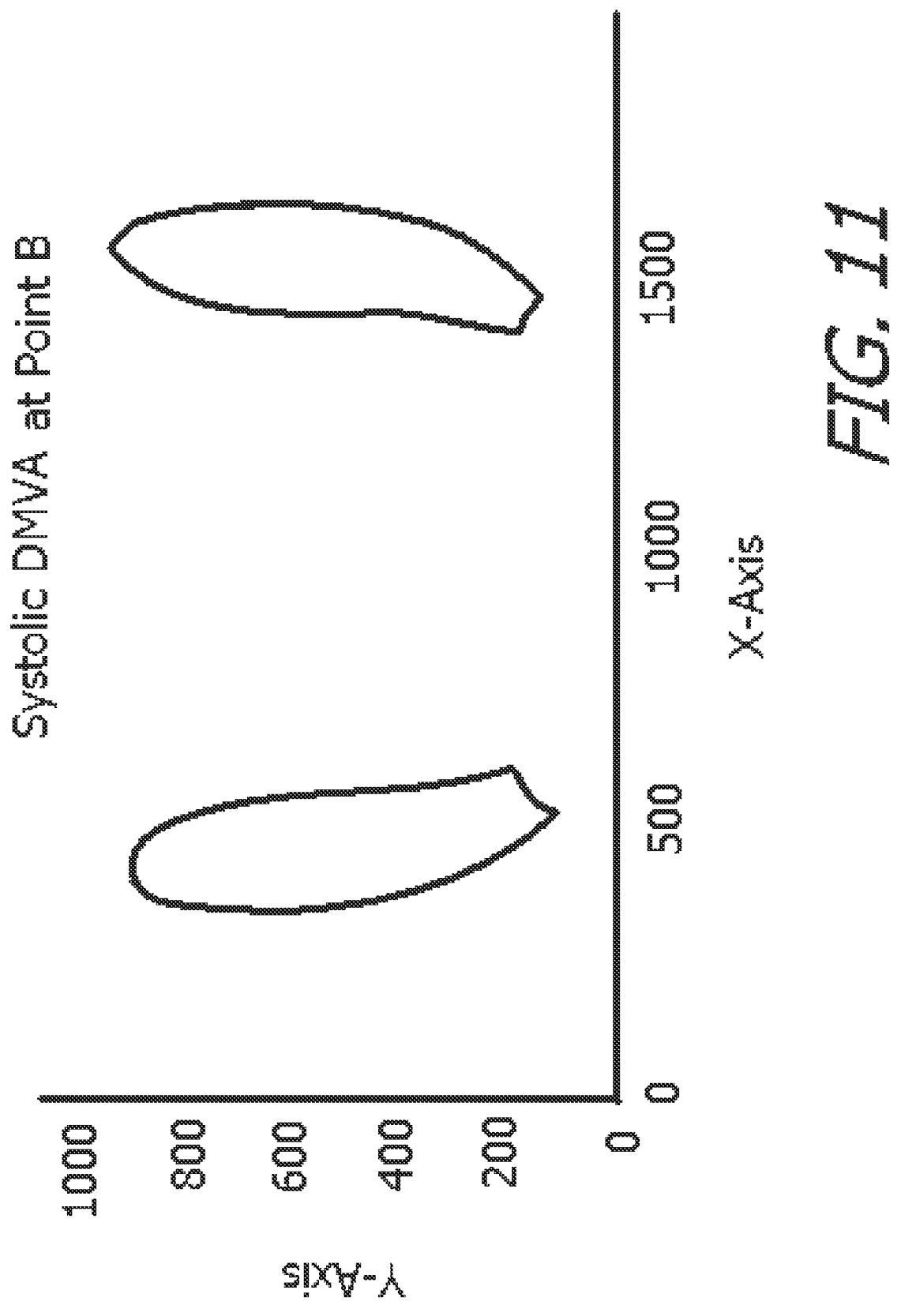
FIG. 11 shows a displacement profile for an exemplary time point along the left ventricle's wall (left side of figure) and the right ventricle's wall (right side of figure) at the end of the systolic or emptying portion of the heart's pump function in a model of the circulatory system.

FIG. 8 shows data collected from an example model of the circulatory system reflecting the primary differences between the right and left ventricular pumping chambers of the heart. Referring to FIG. 8, it can be seen that the Direct Mechanical Ventricular Activation (DMVA) pressure applied to the example left ventricle and the right ventricle has a direct effect upon the hemodynamics of the heart 11 during the time (t) of the heart pump cycle. Referring to FIG. 9 in conjunction with FIG. 8 and FIG. 3, it can be seen that as forces are applied to the heart 11 during the heart pump cycle (t1-tn) both the example left ventricle and the right ventricle undergo complex displacements that are indicative of their strain characteristics. FIG. 10 shows displacements in selected points at various times during the heart pump cycle (t1-tn) on a heart model. The selected point displacements show expansion, or filling, and contraction, or emptying, of the ventricles. However, the displacements alter in both the x-axis and y-axis, therein showing the existence of twisting in addition to expansion, contraction, elongation and shortening. These same displacements occur in the inflatable membranes and outer shell inner of the device. In FIG. 8, there is a point A that corresponds to the end of the systolic, or contraction, pumping cycle. There is also a second point B that indicates a change in the diastolic or expansion pumping cycle. The selected point displacements isolated for the device's inflatable membrane and outer shell, the end of diastolic cycle (point B), are shown in FIG. 10. The selected point displacements isolated for the inflatable membranes and outer shell of the device at the end of the systolic cycle (point A) are shown in FIG. 11.

Figure 12:
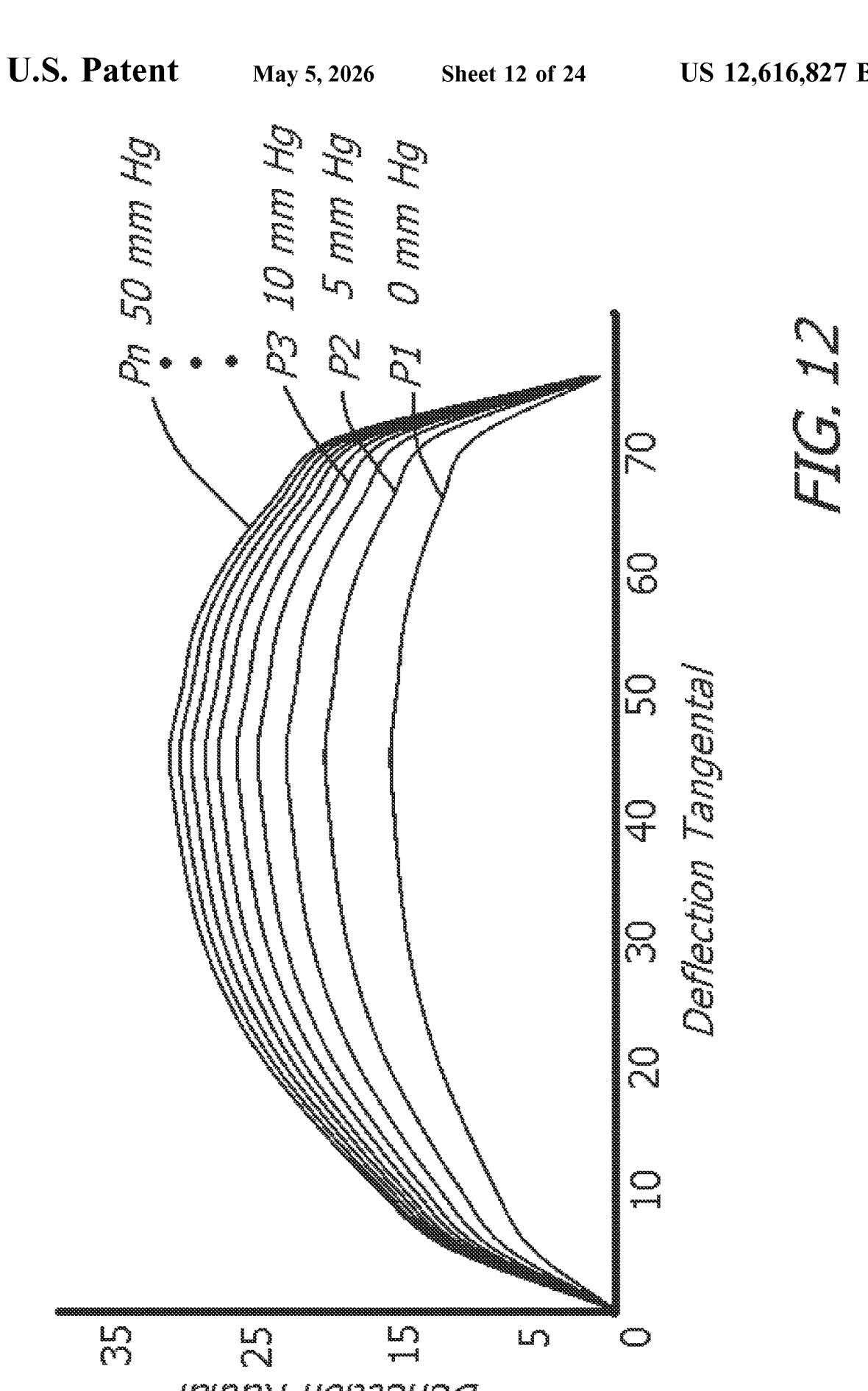
FIG. 12 shows radial versus tangential displacement profiles of an inflatable inner membrane along a long axis in an unloaded condition from the apical attachment point to the basal attachment point along the x-axis at different static drive pressures, wherein the device is not acting on the heart's surface.
Figure 13:
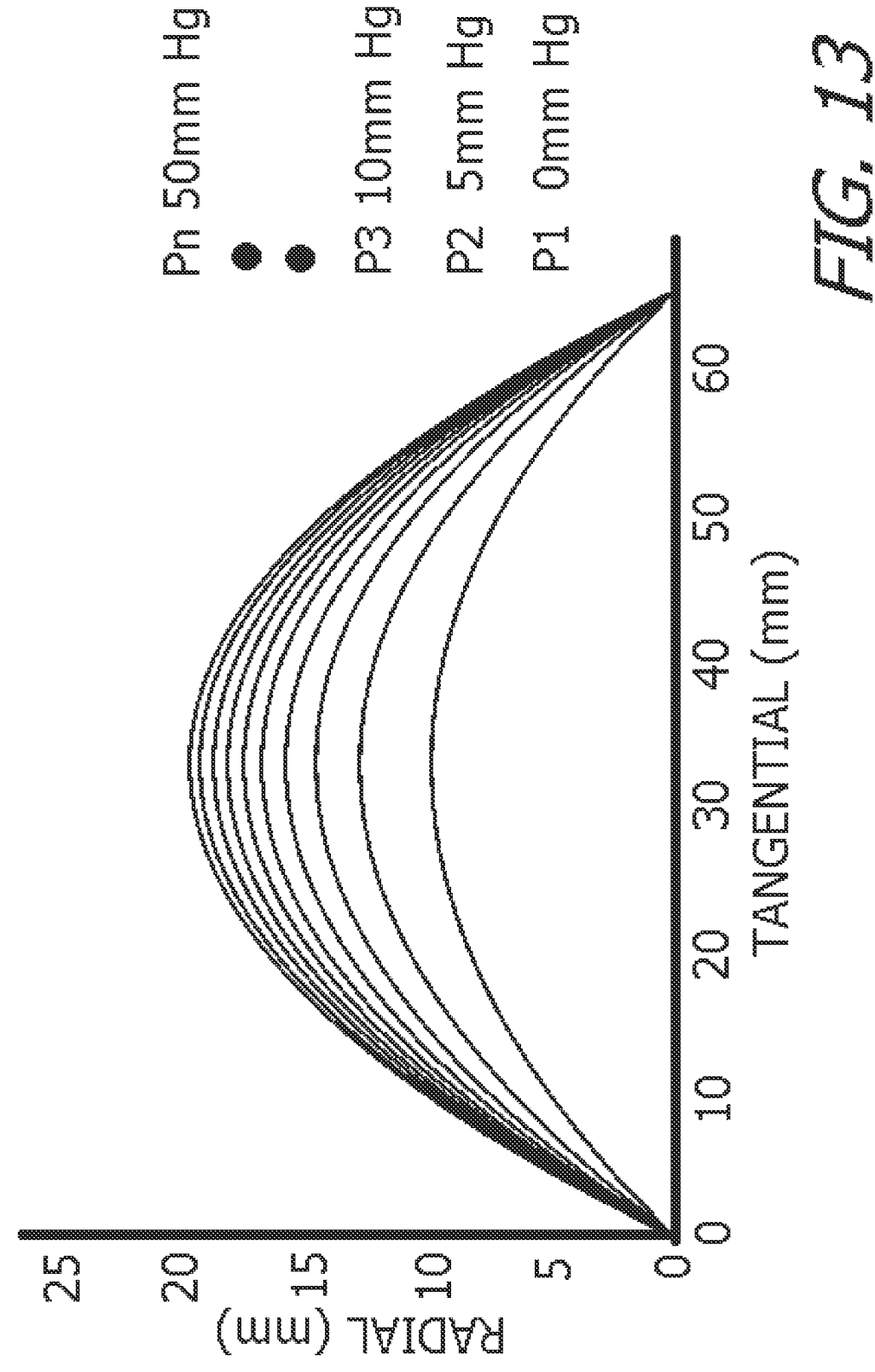
FIG. 13 shows radial and tangential displacement profiles of an inflatable inner membrane along a short axis in an unloaded condition at different static drive pressures, wherein the device is not acting on the heart's surface.

As previously stated, as the inflatable membranes 16 are inflated, the inflatable membranes 16 stretch in a radial direction and in a tangential direction. Referring to FIG. 12 and FIG. 13 in conjunction with FIG. 6, displacements are represented graphically as displacements along the radial, or short axis, direction and to the tangential, or long axis, direction. These representative displacements are shown as determined by measuring both the radial, or short, axis and the tangential to the long axis of the inflatable membrane 16 as the inflatable membrane 16 expands under selected pressures in an unloaded condition. The inflatable membrane 16 used to produce the data is from a 110 mm cup structure, which is herein deemed to represent an average size. As can be seen, the displacement along the long axis (FIG. 13) and the short axis (FIG. 14) of the inflatable membrane 16 varies as a function of inflation pressure. The displacement in the long axis is determined using the following equation:

$$LA(x_i) = K * \left[ -2E - 08x_1^6 + 4E - 06x_1^5 - \right. \qquad \text{Equation 1}$$
$$\left. 0.0003x_1^4 + 0.0132x_1^3 - 0.2748x_1^2 + 3.3624x_1 + 2.2423 \right]$$

The displacement in the short axis is determined using the following equation:

$$SA(x_2) = \qquad \text{Equation 2}$$
$$K * \left[ -8E - 06x_2^4 + 0.001x_2^3 - 0.0529x_2^2 + 1.5781x_2 - 0.2884 \right]$$

In equation 1 and equation 2, (K*) is a conversion factor that is dependent upon the inflation pressure differential (p), where:

$$K(P) = (6.9725 \ln(P) + 5.0464)/32.43$$

Accordingly, it will be understood that displacements in the radial and tangential directions are directly affected by inflation pressure. Changes in inflation pressure over time constitute the pressure profile provided to the inflatable membranes 16.

Figure 14:
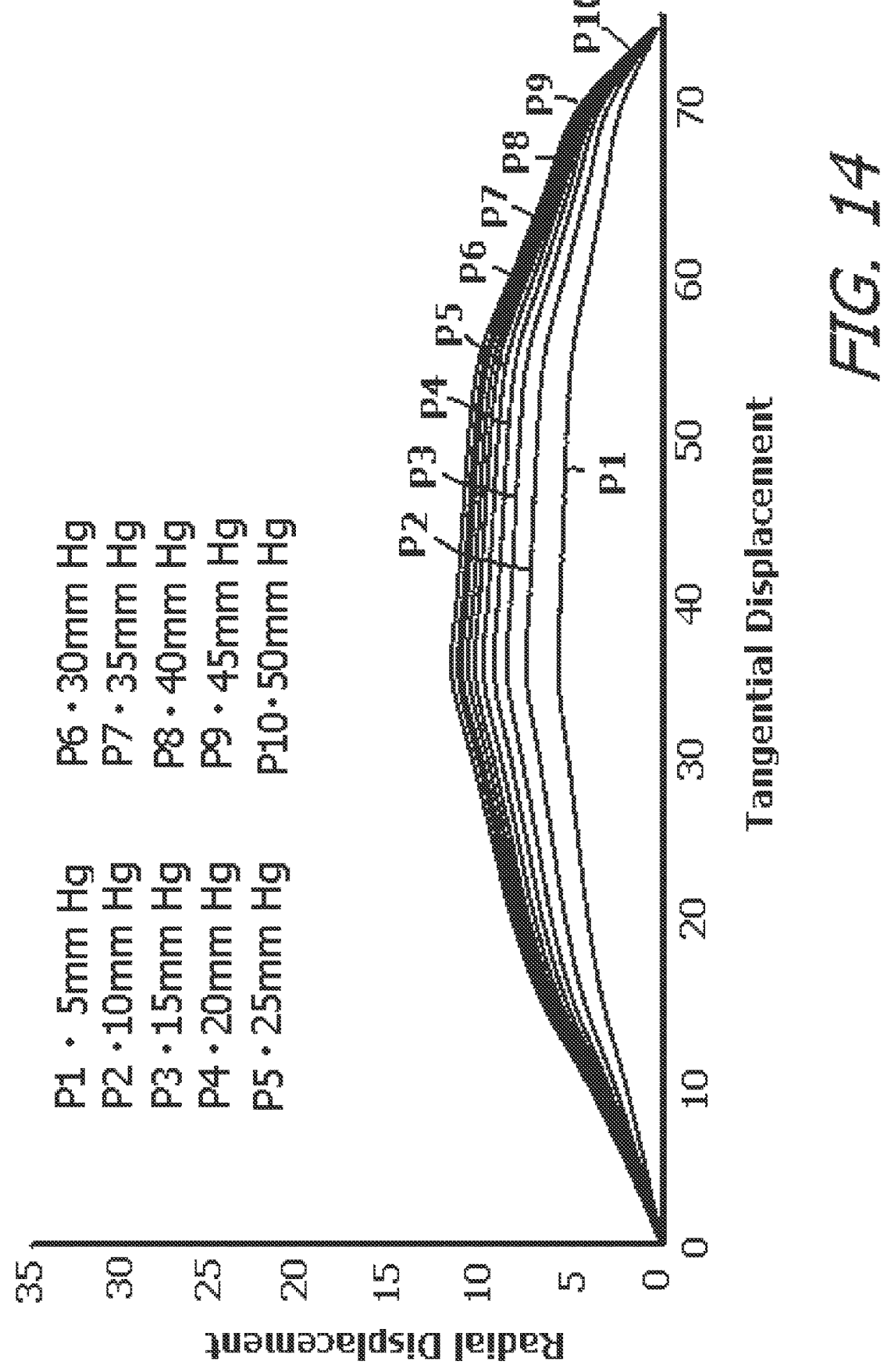
FIG. 14 shows radial and tangential displacement profiles of an outer shell in an unloaded condition in which the device is not acting on the heart's surface at different static drive pressures.

Referring to FIG. 14, it can also be seen that changes to the pressure profile within the inflatable membranes 16 also creates radial and tangential displacements to the long axis of the outer shell 14. As such, each change in pressure creates displacements in the inflatable membranes 16 and the outer shell 14, wherein the displacements are converted into multidirectional forces that are applied to the exterior of the heart 11.

Returning to FIG. 4 and FIG. 5, it will now be understood that the forces applied by the outer shell 14 are indirectly applied to the heart 11. The outer shell 14 applies secondary forces to the inflatable membranes 16 that then transfer those forces to the heart 11. The outer shell 14 is made from elastomeric material 18. As such, the outer shell 14 can expand, contract, elongate, shorten and twist to better provide the complex movements shown in FIGS. 9, 10 and 11. As the inflatable membranes 16 are inflated and expand, the outer shell 14 also expands. As a result, the outer shell 14 applies secondary force interactions to the inflatable membranes 16 that are transferred to the heart 11. The secondary force interactions applied by the outer shell 14 are primarily determined by the elastomeric material 18 used to construct the outer shell 14 and the thickness of the elastomeric material 18 at different points.

By selectively altering the material and/or localized thicknesses of the inflatable membranes 16, a multitude of membrane strain characteristics can be obtained. Likewise, by altering the material and/or area thicknesses of the outer shell 14, a multitude of outer shell strain characteristics can be obtained. Both the strain characteristics of the inflatable membranes 16 and the strain characteristics of the outer shell 14 react to the pressure profile supplied to the inflatable membrane 16 at any given point in time.

In FIG. 4 and FIG. 5, it can be seen that during the systolic, or expansion, phase of the heart pumping cycle, the membranes 16 are inflated. As the inflatable membranes 16 fill and expand, the inflatable membranes 16 apply a force profile to the exterior of the heart 11. The expansion of the inflatable membranes 16 also applies equal and opposite forces to the outer shell 14. The elastomeric material 18 of the outer shell 14 resists the displacement, therein applying secondary forces to the inflatable membranes 16. The secondary forces are transferred through the inflatable membranes 16 to the heart 11. As a consequence, during the systolic cycle, the contraction of the heart 11 is assisted by the complex forces being applied. The forces are dependent upon the elastic strain characteristics of the outer shell 14, the elastic strain characteristics of the inflatable membranes 16, and the pneumatic pressure profile used to pressurize the inflatable membranes 16.

Figure 15:
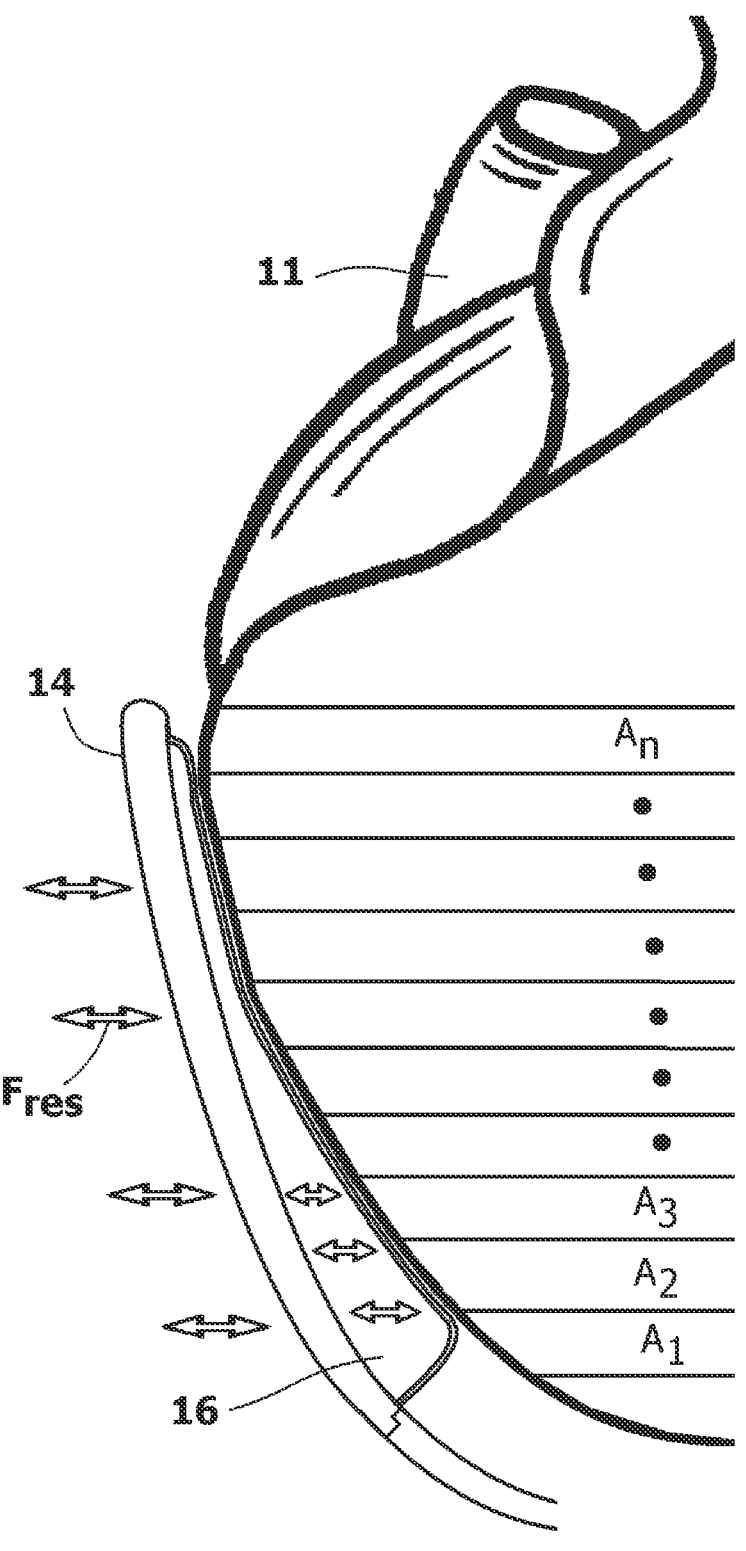
FIG. 15 exemplifies the forces applied to expand or fill the heart by the cardiac assist system during the diastolic cycle of the heart.

Referring to FIG. 15, it will be understood that during the diastolic, or filling, phase of the heart pump cycle, the heart 11 expands. The expansion of the heart 11 is to be assisted, not resisted. To assist the heart 11, the inflatable membranes 16 are deflated. This creates a reduced pressure between the exterior of the heart 11 and the interior of the outer shell 14. The reduced pressure helps the heart 11 expand. The elastomeric material of the inflatable membranes 16 adhere to the tissue of the heart due to surface adhesion forces that are inherent between smooth surfaces in a wet environment. The result is that the inflatable membranes 16 physically pull upon the heart 11 as they deflate. This assists the heart's ability to expand.

The reduced pressure between the heart 11 and the outer shell 14 also acts to contract the outer shell 14. The outer shell 14 yields slightly but is stiff enough to resist being pulled against the expanding heart 11 with a resiliency force $F_{res}$. Accordingly, the forces that help the heart 11 expand are functions of the elastic strain characteristics of the outer shell 14, the elastic strain characteristics of the inflatable membrane 16 and the pneumatic pressure profile used to pressurize the inflatable membranes 16.

Figure 16:
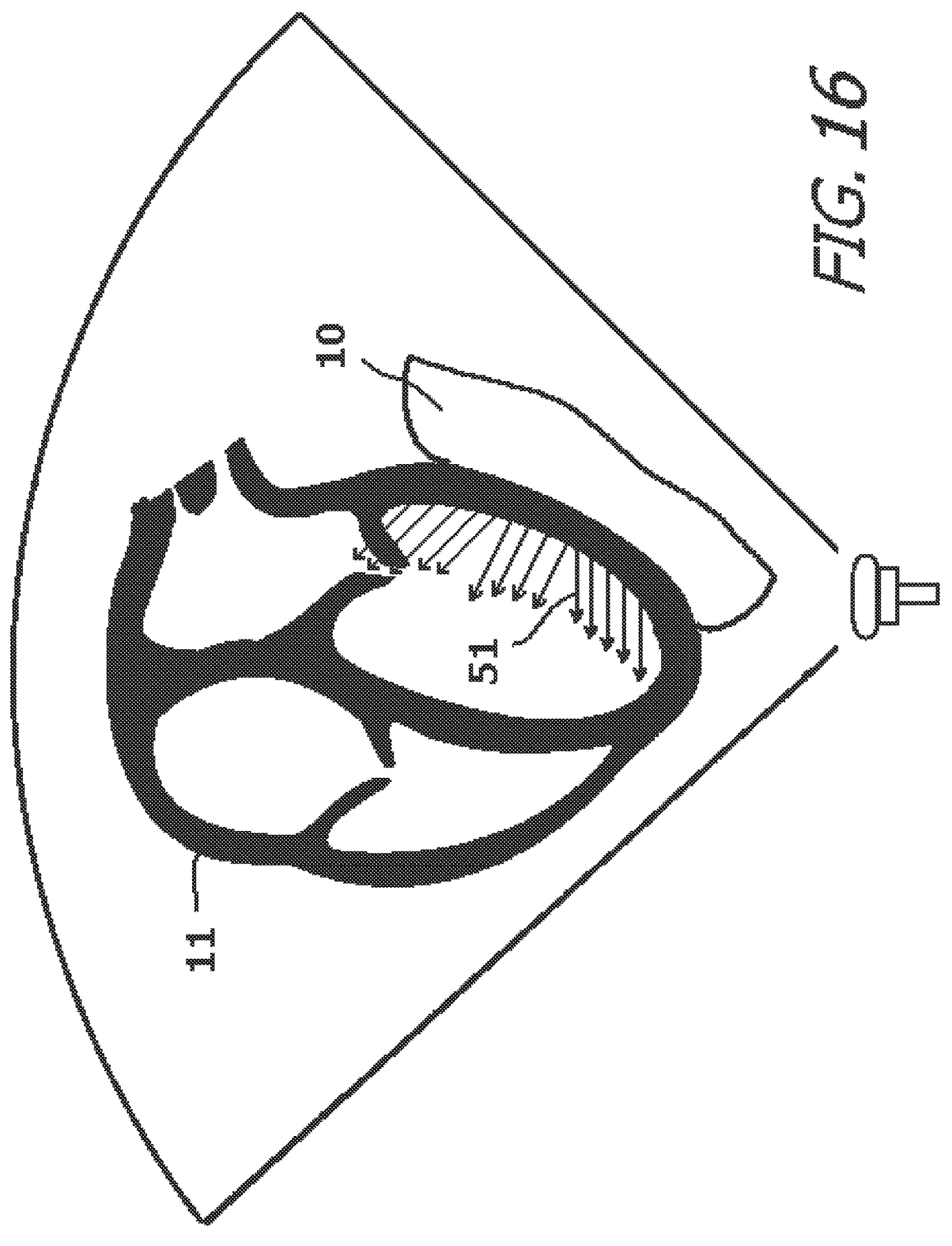
FIG. 16 shows a representation of an ultrasonic scan of the heart overlayed with software calculated directional velocity vectors of the heart's strain.

Referring to FIG. 16, an image representing an ultrasound scan of the heart 11 is shown. The image shows a section of the cardiac assist device 10 acting upon the heart 11. Using commercially available medical scan analysis software, velocity vectors 51 can be calculated that show how far and how fast various points on the heart 11 are expanding and contracting. The velocity vectors 51 also show the changing directions of movement.

Figure 17:
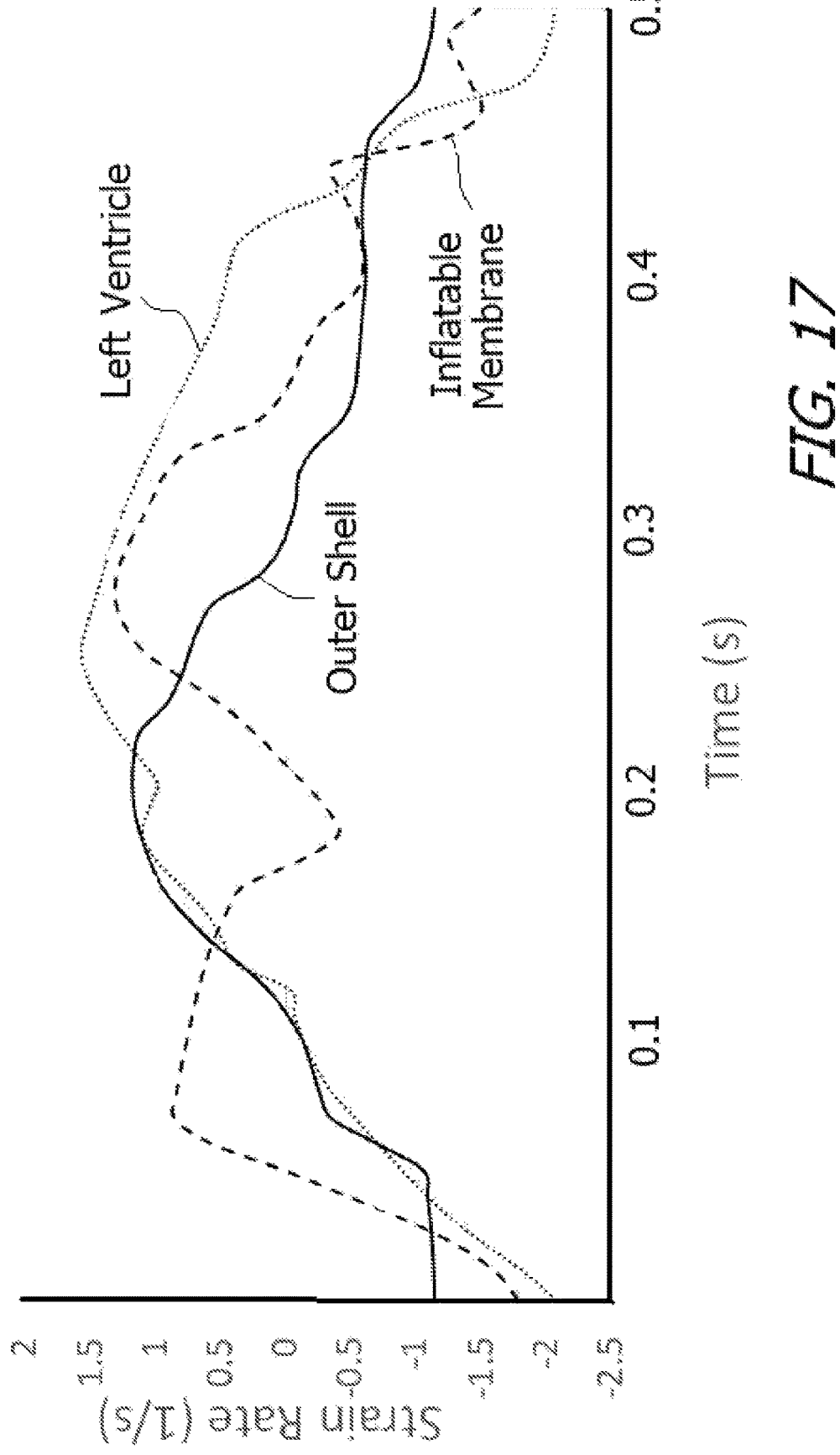
FIG. 17 shows the strain rate waveforms over the period of one heart pump cycle in the mid regions of the heart's left ventricle, the device inflatable membrane, and the device outer shell as measured on a model of the circulatory system.
Figure 18:
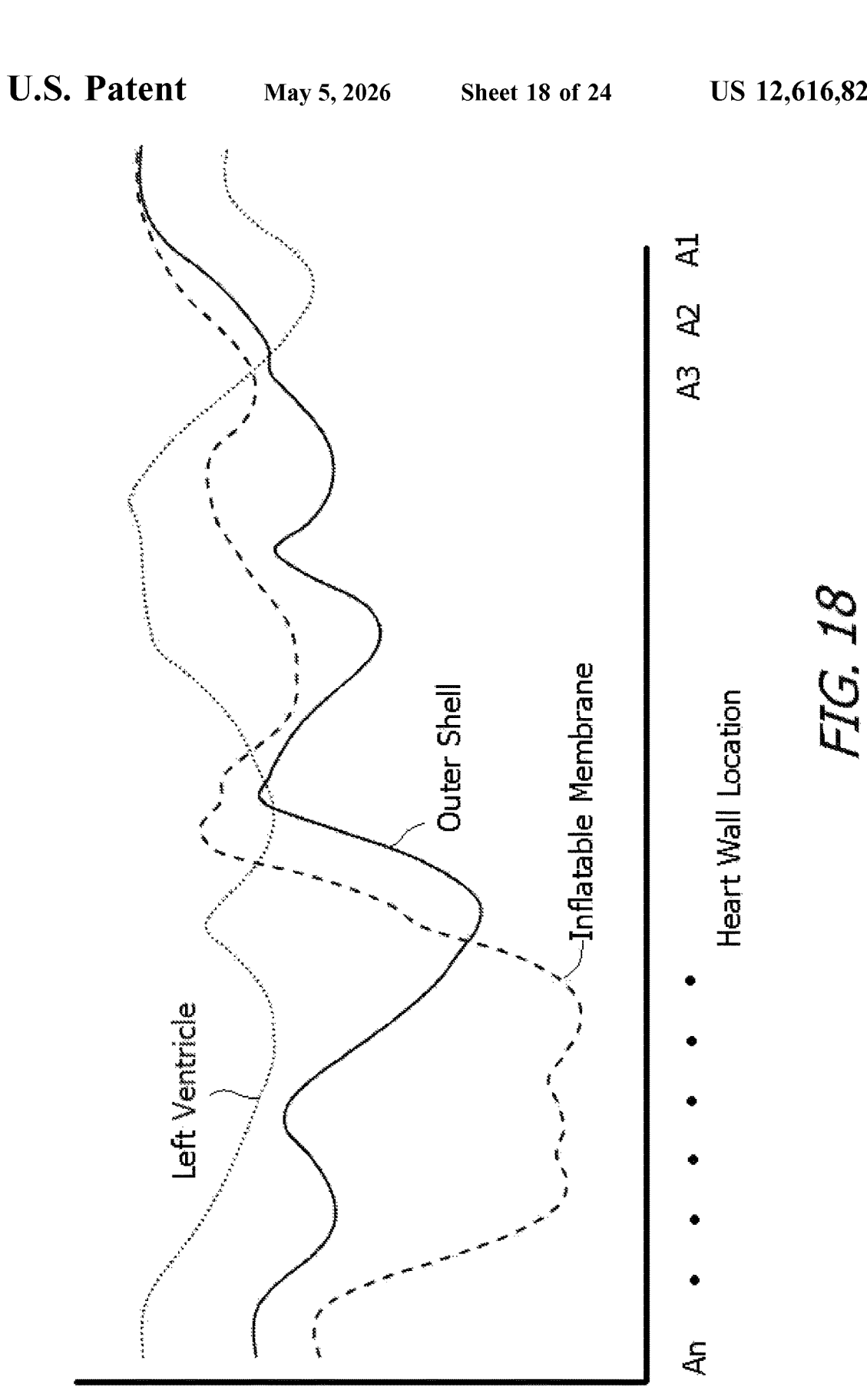
FIG. 18 is a graph that plots peak compression or systolic strain percentage versus heart's position for the long axis of the left ventricular wall, and corresponding locations along the device's inflatable membrane and outer shell with the base of the heart on the left and the apex on the right as measured on a model of the circulatory system.

Using the velocity vectors 51, a variety of data groups can be obtained that are useful in determining if the cardiac assist device in use is proper and effective. Changes in velocity vectors 51 at any point over time can be used to determine strain rate. In FIG. 17, a strain rate waveform is shown that plots the strain rate over time for the inflatable membrane, the outer shell, and the left ventricle. Referring to FIG. 18 in conjunction with FIG. 3 and FIG. 7, the peak strain percentage for the inflatable membrane 16, the outer shell 14 and the left ventricle of the heart 11 are plotted for different areas ($A_1$-$A_n$) of the heart 11.

Figure 19:
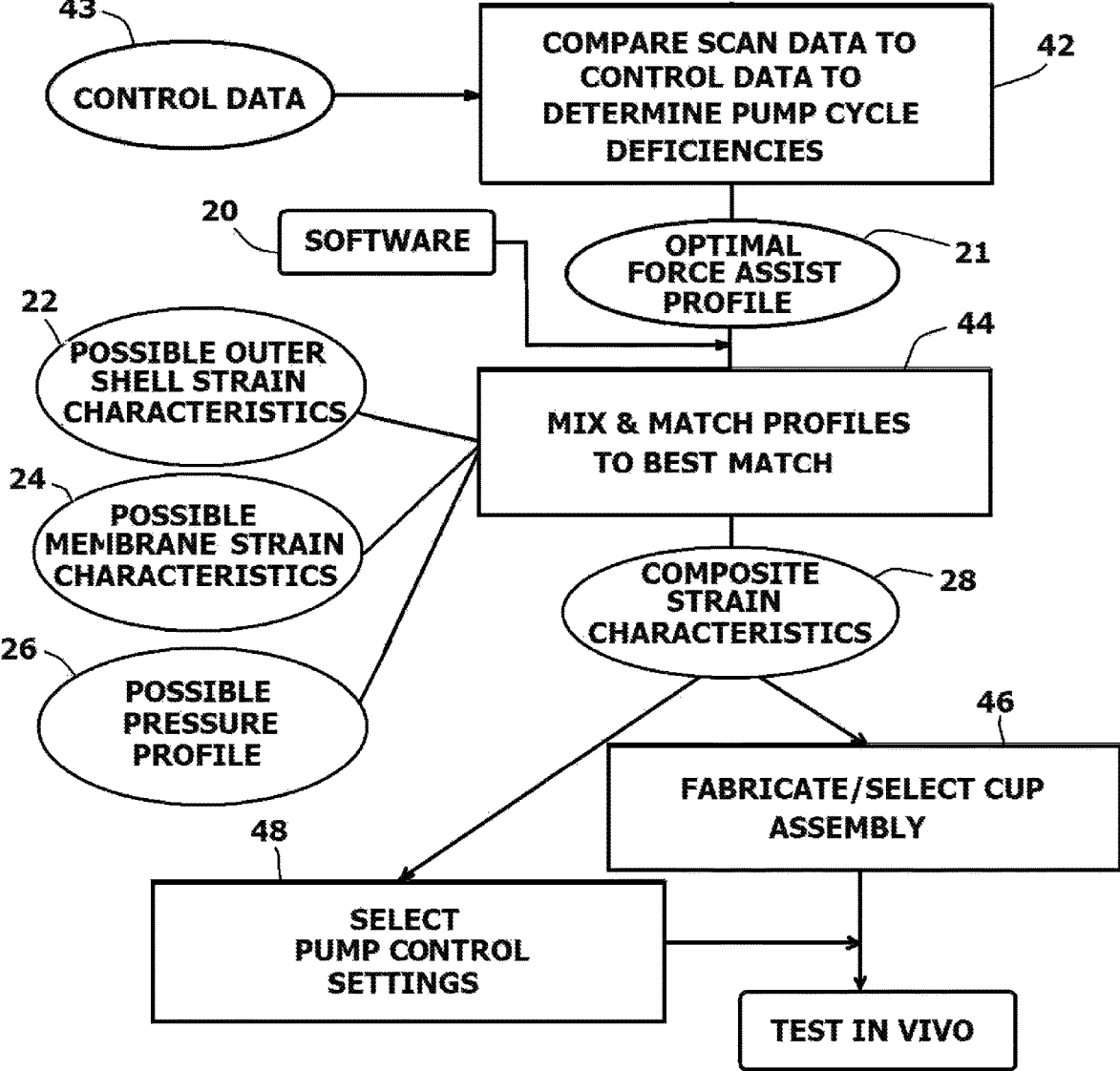
FIG. 19 shows a block diagram logic flow outlining the method of utilizing the present invention cardiac assist system.

Referring to FIG. 19 in conjunction with FIG. 1, it will be understood that to utilize the cardiac assist system 10, a patient is scanned to determine the deficiencies in the pumping ability of the heart 11. Such a determination can be made using standard medical monitoring and/or scanning equipment to determine the pumping characteristics of the heart 11 and comparing that data to a set of control data 43, which is the pumping characteristics of a comparable healthy heart. See Block 42. The pumping characteristics of a healthy heart are known for hearts of different patient types. Alternatively, control data 43 for heart pumping characteristics can be readily calculated by measuring heart dimensions that are obtainable from medical imaging of the heart. The method of calculating strain characteristics for a heart is described in detail in U.S. patent application Ser. No. 17/825,343, the disclosure of which has been incorporated by reference.

Once the pumping deficiencies of the heart 11 are known, an optimal force assist profile 21 is calculated. The force assist profile 21 determines what degrees of force need to be applied to different areas ($A_1$-$A_n$) of the heart 11 during the diastolic and systolic cycles to assist the heart 11 in pumping without further damaging the heart 11. Once the force assist profile 21 is determined, software 20 is used to mix and match the possible outer shell strain characteristics 22, the possible membrane strain characteristics 24, and different pressure profiles 26. The software 20 mixes and matches the profile data until composite strain characteristics 28 are found that best matches the optimal force assist profile 21 required by the heart 11. See Block 44. Once the proper composite strain characteristics 28 are determined, the data is used to fabricate or select a proper cup assembly 12 and to select the proper pump control settings. See Block 46 and Block 48. The pump control settings are used to program the pneumatic pump 15 wherein the pneumatic pump 15 generates the selected pressure profile 26 utilized by the software 20.

Once the cup assembly 12 is installed, the effects of the cup assembly 12 on the heart 11 are monitored. If the effects on the heart 11 in vivo do not match the optimal force profile offered by the cup assembly, then the pump control settings can be adjusted. If the pump control settings are inadequate to correct any deficiencies, the cup assembly 12 is replaced.

Figure 20:
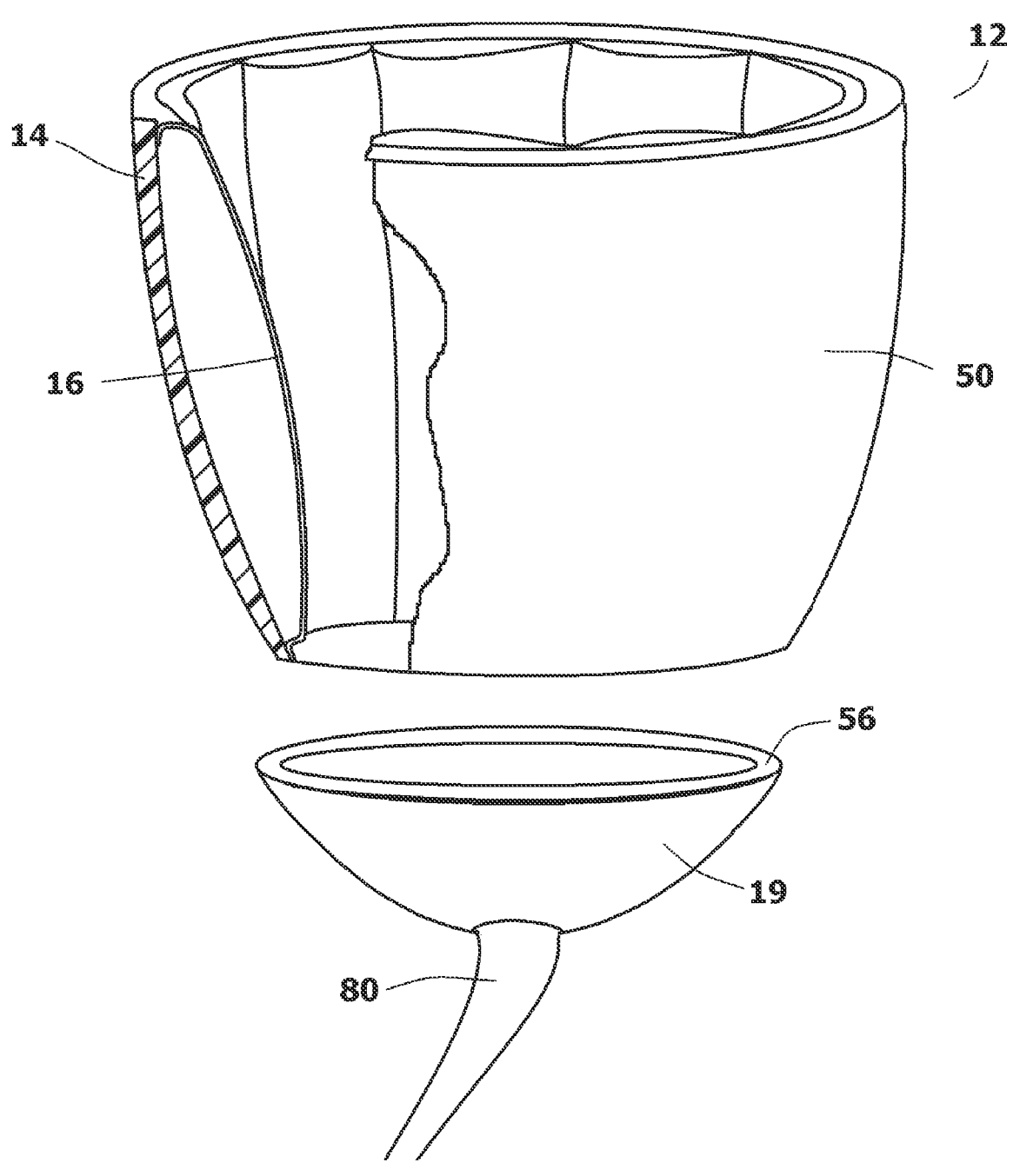
FIG. 20 shows an exploded view of the cup assembly used within the cardiac assist system.

Referring to FIG. 20, in conjunction with FIG. 1 and FIG. 2, it can be seen that the cup assembly 12 consists of a cuff wall 50 and the base 19. The cuff wall 50 is comprised of the outer shell 14 and one or more inflatable membranes 16. The more inflatable membranes 16 that are present, the more variety there is in procuring composite force profiles. The base 19 is concave below a rim 56 that attaches to the cuff wall 50. The base 19 is also made of elastomeric material that allows the base 19 to be elastically deformed. A pressure line 80 attaches to the base 19 for connecting the cup assembly 12 to a pneumatic pump. The pneumatic pump provides positive pressure to inflate the inflatable membranes 16 and negative pressure to help the cup assembly 12 pass onto the heart 11 and remain in place.

Figure 21:
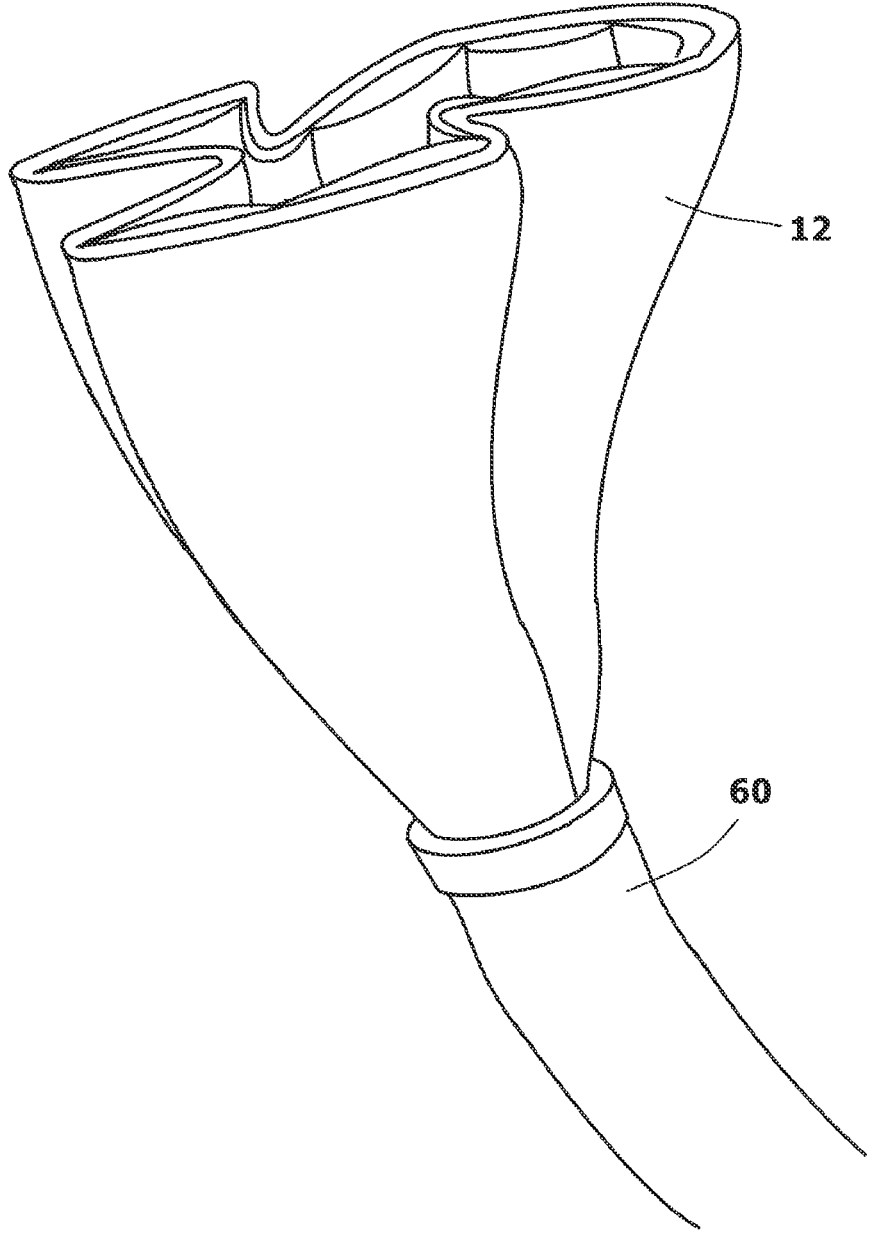
FIG. 21 shows the cup assembly of FIG. 20 in a collapsed configuration while exiting a surgical insertion tube.

Referring to FIG. 21, it will be understood that since the primary components of the cup assembly 12 are made from elastomeric material, the cup assembly 12 is capable of temporarily being collapsed. Accordingly, the cup assembly 12 is capable of being placed in a surgical insertion tube 60 and introduced into the chest cavity through a much smaller incision than is possible for a traditional Anstadt cup.

Figure 22:
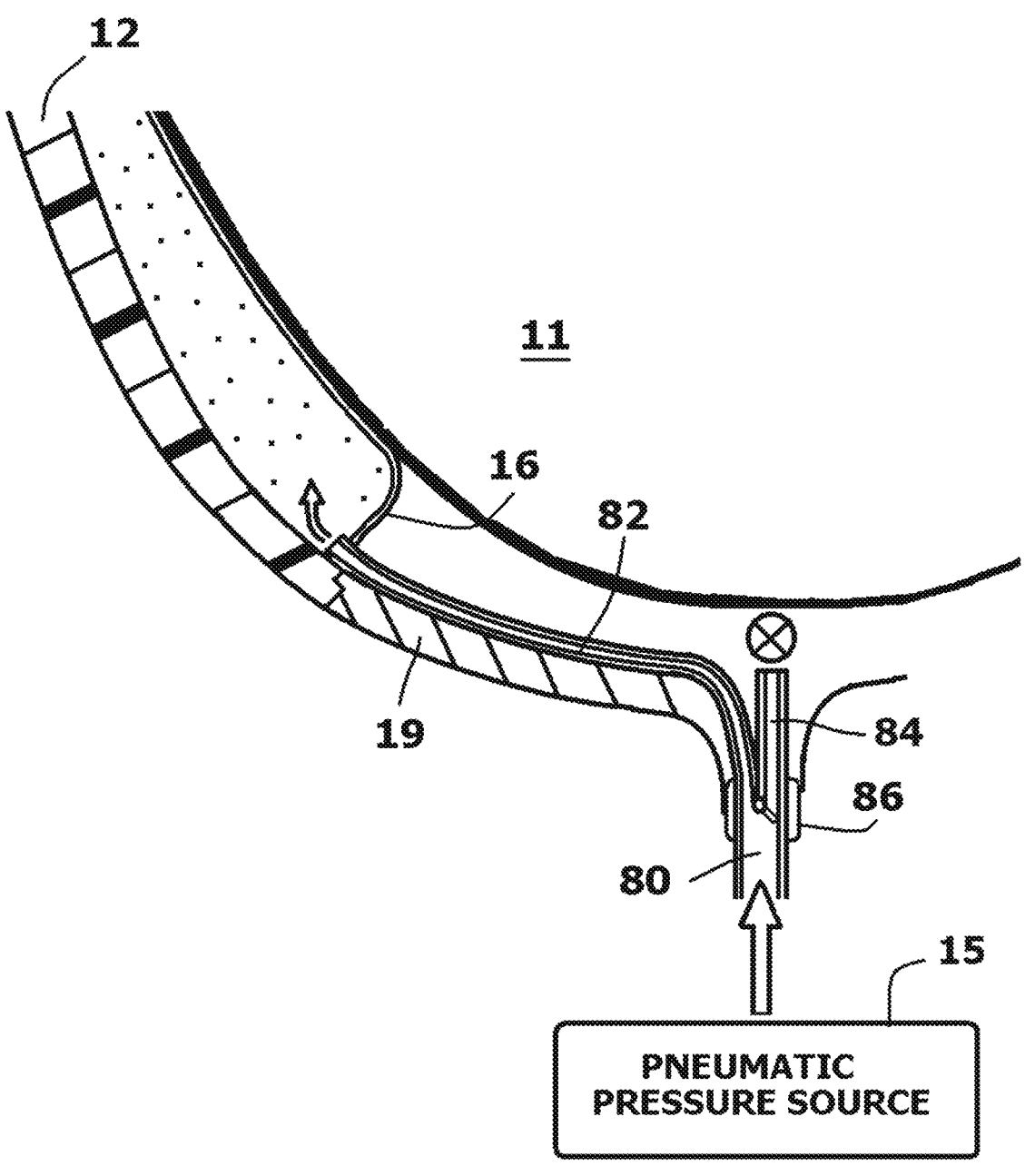
FIG. 22 is a fragmented cross-sectional view of the components that enable pressure to inflate into the inflatable membranes without effecting the vacuum seal.

Referring to FIG. 22, details of how the inflatable membranes 16 are inflated and deflated are provided. A single pressure tube 80 is used to interconnect the cup assembly 12 to the pneumatic pump 15. The pneumatic pump 15 is programmable and can produce various positive and negative pressures relative to ambient air pressure. A unique system is shown that enables the single pressure tube 80 from the pneumatic pump 15 to both pressurize the inflatable membranes 16 and to maintain a negative pressure in the base 19, using only one pressure tube 80. A negative pressure must be maintained between the heart 11 and the base 19 in order to maintain operational contact.

In FIG. 22 it can be seen that inside the base 19, two pneumatic pathways 82, 84 are fed by the single pressure tube 80. The first pneumatic pathway 82 terminates inside an inflatable membrane 16. The second pneumatic pathway 84 terminates inside the base 19, between the base 19 and the heart 11. A valve 86 is provided that enables gas from the pressure tube 80 to pass into the inflatable membrane 16 and inflate the inflatable membrane 16. The valve 86 prevents gas from flowing through the second pneumatic pathway 84 when the pressure in the pressure tube 80 is greater than the pressure in the space between the heart 11 and the base 19. In this manner, when the pressure provided by the pressure tube 80 is above ambient, the gas provided is used exclusively to inflate the inflatable membranes 16. The pressure between the base 19 and the heart 11 remains below ambient pressure.

Figure 23:
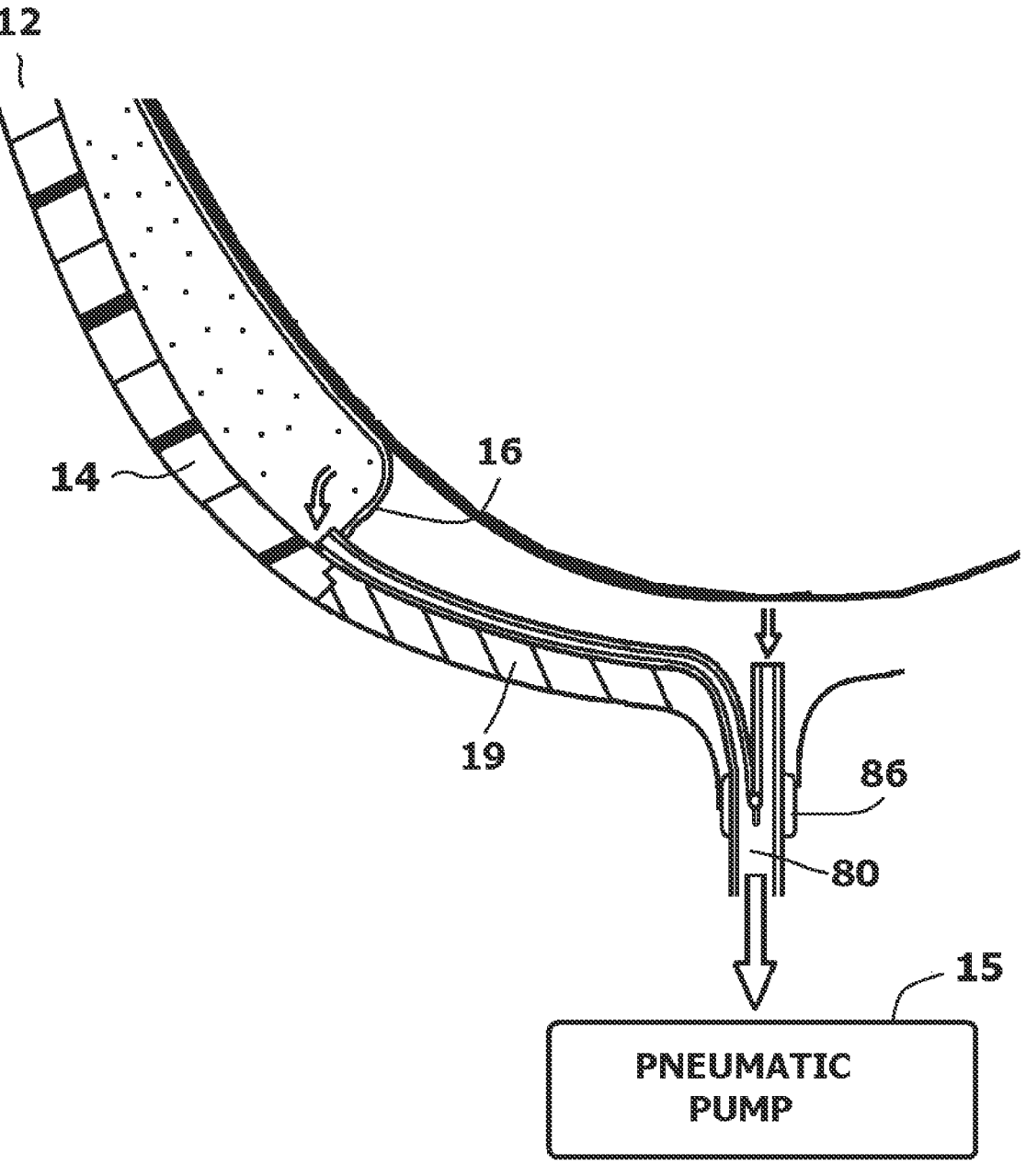
FIG. 23 is a fragmented cross-sectional view of the components that enable pressure to leave both the inflatable membranes and the gap space between the heart and base of the cup structure.

Referring to FIG. 23 in conjunction with FIG. 22, it can be seen that when the pressure in the single pressure tube 80 falls below ambient pressure, the valve 86 opens. As such, the inflatable membranes 16 can be selectively deflated while reestablishing the negative pressure between the base 19 and the heart 11.

The use of a single pressure tube 80 is highly advantageous since it is much less cumbersome than using multiple leads. In this manner, there is greater visibility during surgery and more room in which a surgeon can manipulate his/her hands and instruments.

Figure 24:
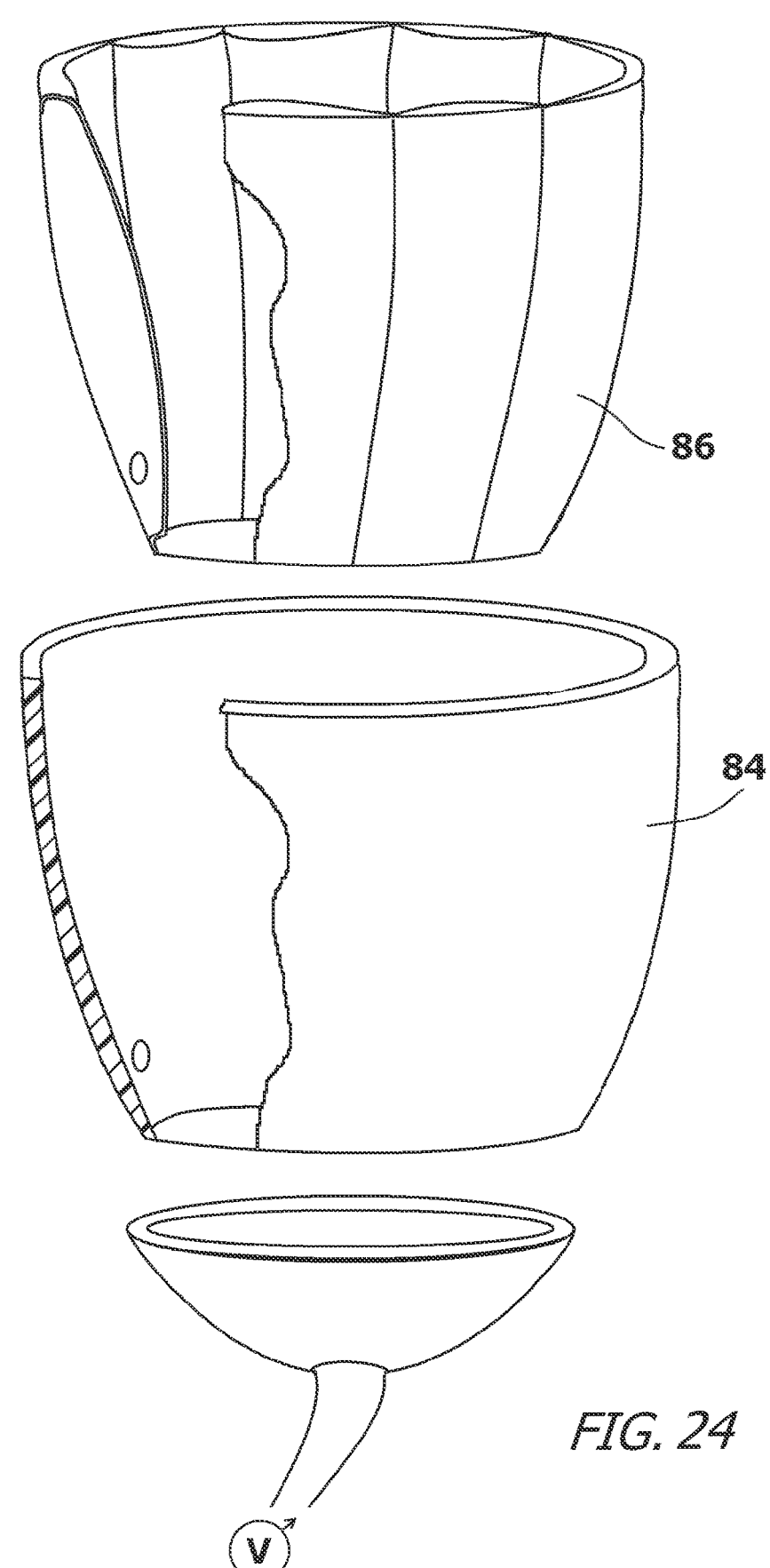
FIG. 24 shows an alternate embodiment of a cardiac assist system.

Referring now to FIG. 24, a variation of the cardiac assist device is shown having an outer shell 84 and inflatable membranes 86 that are detachable. In this manner, various standardized outer shells and inflatable membranes can be selectively mixed and matched to better meet the composite force profile required for the cardiac assist system.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A cardiac assist device, comprising:
a base having a rim and a base apex, wherein said base has a base height between said rim and said base apex;
an outer shell having an open top, wherein said open top is positioned atop said rim of said base therein forming a cup assembly for receiving a portion of a heart therein, said cup assembly having an overall height from said base apex to said open top, wherein said base height is between twenty-five percent and thirty-five percent of said overall height,
wherein said outer shell is made, at least in part, from elastomeric material that enables said outer shell to be able to elastically expand, contract, elongate, shorten and/or twist, wherein said outer shell has an inner surface; and
at least one inflatable membrane lining only said inner surface of said outer shell, wherein said at least one inflatable membrane is connected to said inner surface of said outer shell along a basal bond that is a first distance from said open top and along an apical bond that is a further second distance from said open top,
wherein said at least one inflatable membrane contacts the heart within the cup assembly as said at least one inflatable membrane is selectively inflated and both said outer shell and said at least one inflatable membrane combine to provide a force assist profile that causes the heart to pump more efficiently when applied to the heart using the cardiac assist device.

2. The cardiac assist device according to claim 1, wherein said at least one inflatable membrane creates elastic displacements in said outer shell when said at least one inflatable membrane is selectively inflated, wherein said elastic displacements in said outer shell generate forces that contribute to said force assist profile.

3. The cardiac assist device according to claim 1, wherein said at least one inflatable membrane is inflated and deflated in accordance with a pressure profile, wherein said pressure profile along with both said outer shell and said at least one inflatable membrane combine to provide said force assist profile.

4. The cardiac assist device according to claim 1, wherein said at least one inflatable membrane is selectively inflated and deflated in accordance with a pressure profile provided by a pneumatic pump.

5. The cardiac assist device according to claim 4, wherein said outer shell embodies outer shell strain characteristics that are a function of dimensions and materials embodied by said outer shell.

6. The cardiac assist device according to claim 5, wherein said at least one inflatable membrane embodies membrane strain characteristics that are a function of dimensions and materials embodied by said at least one inflatable membrane.

7. The cardiac assist device according to claim 6, wherein said force assist profile is a function of said outer shell strain characteristics, said membrane strain characteristics, and said pressure profile.

8. The cardiac assist device according to claim 1, wherein said first distance of said basal bond is a distance below the open top that is no greater than five percent of said overall height.

* * * * *